(12) United States Patent
Jensen et al.

(10) Patent No.: US 7,857,978 B2
(45) Date of Patent: Dec. 28, 2010

(54) MEMBRANE FOR FILTERING OF WATER

(75) Inventors: Peter Holme Jensen, Copenhagen (DK); Danielle Keller, Odense (DK); Claus Hélix Nielsen, Taastrup (DK)

(73) Assignee: Aquaporin A/S, Copehhagen N (DK)

( * ) Notice: Subject to any disclaimer, the term of this patent is extended or adjusted under 35 U.S.C. 154(b) by 0 days.

(21) Appl. No.: 11/915,121

(22) PCT Filed: May 19, 2006

(86) PCT No.: PCT/DK2006/000278

§ 371 (c)(1),
(2), (4) Date: May 12, 2008

(87) PCT Pub. No.: WO2006/122566

PCT Pub. Date: Nov. 23, 2006

(65) Prior Publication Data

US 2009/0120874 A1 May 14, 2009

Related U.S. Application Data

(60) Provisional application No. 60/683,466, filed on May 20, 2005, provisional application No. 60/718,890, filed on Sep. 20, 2005.

(30) Foreign Application Priority Data

May 20, 2005 (DK) .......................... PA 2005 00740
Sep. 20, 2005 (DK) .......................... PA 2005 01309

(51) Int. Cl.
B01D 69/02 (2006.01)

(52) U.S. Cl. ...................... 210/652; 210/650; 210/651; 210/653; 210/655; 210/500.1; 210/500.29; 210/641; 210/321.75; 422/101; 424/450

(58) Field of Classification Search ............ 210/500.35, 210/500.36, 500.42, 641, 321.75, 257.2, 210/500.2, 7, 490, 650–653, 655, 500.1, 210/500.29, 900; 435/17.1, 4; 436/524, 436/172, 82.05; 530/402; 425/450, 1.21, 425/9, 32, 417, 489; 264/4.1, 4.3, 4.6, 41; 424/450; 977/713–714, 718; 422/101
See application file for complete search history.

(56) References Cited

U.S. PATENT DOCUMENTS 3,906,250 A 9/1975 Loeb (Continued)

FOREIGN PATENT DOCUMENTS

| EP | 1885477 B1 | 2/2010 |
| WO | WO 02/13955 | 2/2002 |
| WO | WO 2004/099088 | 11/2004 |
| WO | WO 2007/033675 | 3/2007 |

OTHER PUBLICATIONS

Coury et al., Reconstintution of water channel function of aquaporins 1 and 2 by expression in yeast secretory vesicles, 1998, The American Physiological Society, pp. F34-F42.*

(Continued)

*Primary Examiner*—Tony G Soohoo
*Assistant Examiner*—David C Mellon
(74) *Attorney, Agent, or Firm*—Kristina Bieker-Brady; Clark & Elbing LLP

(57) ABSTRACT

Disclosed are novel water membranes comprising lipid bilayers incorporating functional aqua-porins. The lipid bilayers are arranged in sandwich structures including hydrophilic or hydro-phobic support materials. Also disclosed are water purification devices/systems, including reverse osmosis filtering devices that include membranes having functional aquaporins. Methods of water purification and methods of preparing the membranes are also disclosed. Further, the invention provides for a new type of perforated, hydrophobic polymer film and to membranes containing lipid bilayers having other transmembrane proteins than aquaporins introduced.

46 Claims, 14 Drawing Sheets

Supported lipid bilayer with incorporated Aquaporin molecules

Porous support of lipid bilayer, like mica, muscovite, mica tape, polysulfon, AlO₃, cellulose or other support with hydrophilic surface.

Planar lipid bilayer membrane with incorporated aquaporins.

Aquaporin molecule

Phospholipid molecule or other amphiphilic lipid molecule

U.S. PATENT DOCUMENTS

| | | | |
|---|---|---|---|
| 4,193,267 A | | 3/1980 | Loeb |
| 4,966,708 A | | 10/1990 | Oklejas et al. |
| 5,741,416 A | | 4/1998 | Tempest, Jr. |
| 6,297,059 B1 * | | 10/2001 | Song et al. .................. 436/501 |
| 7,563,370 B2 | | 7/2009 | Thorsen et al. |
| 7,566,402 B2 | | 7/2009 | Thorsen et al. |
| 7,713,544 B2 * | | 5/2010 | Chaikof et al. .............. 424/450 |
| 2001/0034432 A1 * | | 10/2001 | Sodroski et al. ............. 530/350 |
| 2002/0107215 A1 * | | 8/2002 | Brown et al. ................. 514/44 |
| 2003/0102263 A1 * | | 6/2003 | Lopez et al. ................ 210/639 |
| 2004/0049230 A1 | | 3/2004 | Montemagno et al. |
| 2007/0087328 A1 * | | 4/2007 | Sleytr et al. ..................... 435/4 |
| 2007/0275480 A1 * | | 11/2007 | Brander et al. ............. 436/501 |
| 2009/0007555 A1 | | 1/2009 | Jensen |
| 2009/0120874 A1 | | 5/2009 | Jensen et al. |
| 2010/0178592 A1 * | | 7/2010 | Cinquin et al. .............. 429/512 |

OTHER PUBLICATIONS

Saparov et al., Water and Ion Permeation of Aquaporin-1 in Planar Lipid Bilayers, Jun. 15, 2001, The Journal of Biological Chemistry, pp. 31515-31520.*

Becker et al., The World of the Cell, 2006, Pearson Benjamin Cummings, Sixth Edition, pp. 171-174,203.*

Tien et al., Planar Lipid Bilayers (BLMs) and their Applications, 2003, Elsevior, Membrane Science and Technology Series 7, pp. 381-382, 450-454, 807-819, 825-829.*

Heyse et al.,"Emerging Techniques for Investigating Molecular Interactions at Lipid Membranes," *Biochimica et Biophysica Acta. Mr. Reviews on Biomembranes*, 1376(3):319-338 (1998).

Mou et al., "Gramicidin A Aggregation in Supported Gel State Phosphatidylcholine Bilayers," *Biochemistry*, 35:3222-3226 (1996).

Reviakine I., Brisson A., "Formation of Supported Phospholipid Bilayers from Unilamellar Vesicles Investigated by Atomic Force Microscopy," *Langmuir*, 16:1806-1815 (2000).

Agre et al., "The Aquaporins, Blueprints for Cellular Plumbing Systems," *J. Biol. Chem.* 273:14659-14662 (1998).

Borgnia et al., "Cellular and Molecular Biology of the Aquaporin Water Channels," *Annu. Rev. Biochem.* 68:425-458 (1999).

Brian et al., "Allogeneic Stimulation of Cytotoxic T Cells by Supported Planar Membranes," *Proc. Natl. Acad. Sci. U.S.A.* 81:6159-6163 (1984).

Burykin et al., "What Really Prevents Proton Transport through Aquaporin? Charge Self-Energy versus Proton Wire Proposals," *Biophys. J.* 85:3696-3706 (2003).

Chakrabarti et al., "Molecular Basis of Proton Blockage in Aquaporins," *Structure* 12:65-74 (2004).

Dainty et al., "Unstirred Layers' in Frog Skin," *J. Physiol.* 182:66-78 (1966).

de Groot et al., "Water Permeation Across Biological Membranes: Mechanism and Dynamics of Aquaporin-1 and GlpF," *Science* 294:2353-2357 (2001).

de Groot et al., "The Mechanism of Proton Exclusion in the Aquaporin-1 Water Channel," *J. Mol. Biol.* 333:279-293 (2003).

Fettiplace et al., "Water Permeability of Lipid Membranes," *Physiological Reviews* 60:510-550 (1980).

Fu et al., "Structure of a Glycerol-Conducting Channel and the Basis for Its Selectivity," *Science* 290:481-486 (2000).

Heymann et al., "Aquaporins: Phylogeny, Structure, and Physiology of Water Channels," *News Physiol. Sci.* 14:187-193 (1999).

Ilan et al., "The Mechanism of Proton Exclusion in Aquaporin Channels," *PROTEINS: Structure, Function, and Bioinformatics* 55:223-228 (2004).

Jensen et al., "Electrostatic Tuning of Permeation and Selectivity in Aquaporin Water Channels," *Biophys. J.* 85:2884-2899 (2003).

Leonenko et al., "Supported Planar Bilayer Formation by Vesicle Fusion: The Interaction of Phospholipid Vesicles with Surfaces and the Effect of Gramicidin on Bilayer Properties Using Atomic Force Microscopy," *Biochim. Biophys. Acta* 1509:131-147 (2000).

Lin et al., "Amyloid β Protein Forms Ion Channels: Implications for Alzheimer's Disease Pathophysiology," *FASEB J.* 15:2433-2444 (2001).

Montal et al., "Formation of Biomolecular Membranes from Lipid Monolayers and a Study of Their Electrical Properties," *Proc. Nat. Acad. Sci. U.S.A.* 69:3561-3566 (1972).

Murata et al., "Structural Determinants of Water Permeation Through Aquaporin-1," *Nature* 407:599-605 (2000).

Pohl et al., "The Effect of a Transmembrane Osmotic Flux on the Ion Concentration Distribution in the Immediate Membrane Vicinity Measured by Microelectrodes," *Biophys. J.* 72:1711-1718 (1997).

Pohl et al., "Highly Selective Water Channel Activity Measured by Voltage Clamp: Analysis of Planar Lipid Bilayers Reconstituted with Purified AqpZ," *Proc. Natl. Acad. Sci. U.S.A.* 98:9624-9629 (2001).

Preston et al., "Appearance of Water Channels in *Xenopus* Oocytes Expressing Red Cell CHIP28 Protein," *Science* 256:385-387 (1992).

Reimhult et al., "Intact Vesicle Adsorption and Supported Biomembrane Formation from Vesicles in Solution: Influence of Surface Chemistry, Vesicle Size, Temperature, and Osmotic Pressure," *Langmuir* 19:1681-1691 (2003).

Ren et al., "Visualization of Water-Selective Pore by Electron Crystallography in Vitreous Ice," *Proc. Natl. Acad. Sci. U.S.A.* 98:1398-1403 (2001).

Rinia et al., "Visualization of Highly Ordered Striated Domains Induced by Transmembrane Peptides in Supported Phosphatidylcholine Bilayers," *Biochemistry* 39:5852-5858 (2000).

Saparov et al., "Water and Ion Permeation of Aquaporin-1 in Planar Lipid Bilayers," *J. Biol. Chem.* 276:31515-31520 (2001).

Simonsen et al., "Structure of Spin-Coated Lipid Films and Domain Formation in Supported Membranes Formed by Hydration," *Langmuir* 20:9720-9728 (2004).

Sui et al., "Structural Basis of Water-Specific Transport Through the AQP1 Water Channel," *Nature* 414:872-878 (2001).

Tajkhorshid et al., "Control of the Selectivity of the Aquaporin Water Channel Family by Global Orientation Tuning," *Science* 296:525-530 (2002).

Tokumasu et al., "Nanoscopic Lipid Domain Dynamics Revealed by Atomic Force Microscopy," *Biophys. J.* 84:2609-2618 (2003).

van Kan et al., "The Peptide Antibiotic Clavanin A Interacts Strongly and Specifically with Lipid Bilayers," *Biochemistry* 42:11366-11372 (2003).

Webber et al., "Hydrodynamic Studies of Adsorbed Diblock Copolymers in Porous Membranes," *Macromolecules* 23:1026-1034 (1990).

Zeidel et al., "Reconstitution of Functional Water Channels in Liposomes Containing Purified Red Cell CHIP28 Protein," *Biochemistry* 31:7436-7440 (1992).

Zhu et al., "Theory and Simulation of Water Permeation in Aquaporin-1," *Biophys. J.* 86:50-57 (2004).

International Search Report from PCT/DK2006/000278, completed Jan. 8, 2007, mailed Jan. 29, 2007.

International Preliminary Report on Patentability from PCT/DK2006/000278, completed Aug. 23, 2007.

Written Opinion of the International Searching Authority from PCT/DK2006/000278, completed Jan. 8, 2007, completed Jan. 29, 2007.

Thesis of Danielle Keller, "Chapter 4: Reconstitution of Cytochrome C Oxidase," pp. 41-45, 2005.

* cited by examiner

Supported lipid bilayer with incorporated Aquaporin molecules

Porous support of lipid bilayer, like mica, muscovite, mica tape, polysulfon, AlO₂, cellulose or other support with hydrophilic surface.

Planar lipid bilayer membrane with incorporated aquaporins.

Aquaporin molecule

Phospholipid molecule or other amphiphilic lipid molecule

Heymann and Engel, *News Physiol. Sci* (1999)

Proteoliposomes → Adsorbed proteoliposomes → Supported bilayer

MEMBRANE FOR FILTERING OF WATER

CROSS-REFERENCE TO RELATED APPLICATIONS

This application is the National Stage of International Application No. PCT/DK2006/000278, filed May 19, 2006, which claims benefit of Denmark Application Nos. PA 2005 00740, filed May 20, 2005, and PA 2005 01309, filed Sep. 20, 2005, and U.S. Provisional Application Ser. Nos. 60/683,466, filed May 20, 2005, and 60/718,890, filed Sep. 20, 2005.

FIELD OF THE INVENTION

The present invention relates to a novel membrane comprising functional aquaporin channels or tetramers suitable for filtering pure water and/or glycerol, a filtering device/purification system comprising such membrane, and methods of using the same for producing ultra pure water and for extracting excess water from aqueous compositions. The invention also relates to novel hydrophobic polymer films.

BACKGROUND OF THE INVENTION

Various water treatment systems and methods have traditionally been developed for purifying natural and polluted water sources to obtain purified water, which is suitable for human and/or animal consumption. In addition, ultra pure water is in high demand from the semiconductor and pharmaceutical industry. The production of ultra pure water demands more specialized filters and chemical treatment of the water source. A number of techniques are used, such as membrane filtration, ion exchangers, sub micron particle filters or nano-filters, ultraviolet light and ozone treatment. The produced water is extremely pure and contains no to very low concentrations of salts, organic components, dissolved gases such as oxygen, suspended solids, and microorganisms such as viruses and bacteria. However, because of factors such as the continuing miniaturization in the semiconductor industry, the specifications for ultra pure water become increasingly stricter.

Traditionally, water is purified or treated through a variety of available water treatment devices designed both for communal and for point-of-use applications, e. g. based on the following technologies: activated carbon for organic removal: ultraviolet light disinfection: ion exchange for hardness removal (water softening), and membrane desalination such as reverse osmosis (RO) or nanofiltration (NF). However, nanofiltration is relatively new in the field of water treatment technology. An NF membrane produces soft water by retaining the hardness creating divalent ions present in water. An NF membrane allows a high percentage of monovalent ions such as sodium and chloride to pass through, while it retains a high percentage of the divalent ions. It is the monovalent ions that create osmotic pressure that requires the moderate to high pressures necessary to pump water through an RO membrane. Therefore, nanofilter membranes require much less pressure to pump water across the membrane because hydraulic driving force does not have to overcome the effect of osmotic pressure derived from monovalent ions. Generally speaking, RO membranes used for residential and commercial water treatment applications remove all dissolved solids by approximately 98%. while nanofilter membranes remove divalent ions (hardness components: calcium and magnesium) by approximately 90% and monovalent ions (sodium chloride) by approximately 50%.

Desalination devices that use membrane elements (for example: RO or NF) always create two streams of water as the water exits the element: desalinated product water (which has passed through the membrane), and a waste brine (that has flowed across the membrane surface). This waste brine stream is necessary to flush salts and minerals away from the membrane to prevent them from accumulating and fouling the membrane surface. If a buildup of salts and minerals in the feed-water to a membrane occurs continuously, dissolved substances can precipitate and form a solid film, fouling the surface of the membrane. In addition, colloidal and particulate contaminants can also adhere to the membrane surface and cause fouling. With many water-borne contaminants, if a membrane becomes irreversibly scaled, or fouled, it cannot be cleaned and must be replaced. This characteristic of membrane processes poses a significant problem in reducing waste effluent especially in point of use (POU) water treatment systems that are typically compact and built as economically as possible.

Ion exchange devices are also used to soften so called "hard water". The problem with ion exchange water softening systems is that they remove the hardness components of water (calcium and magnesium ions) by exchanging them for sodium ions in order to create what is called "soft water". When regeneration of the ion exchange media takes place, a concentrated water stream of sodium, chloride, calcium and magnesium ions goes into the sewer system creating an environmental waste disposal problem. An example of a water purification system of such type is described in U.S. Pat. No. 5,741,416 for "water purification system having plural pairs of filters and an ozone contact chamber", disclosing a water purification system that is effective to oxidize organic contaminants and to destroy most of the bacteria, viruses, and other microbes in such water stream. Systems involving dialysis membranes that are selective for monovalent cations have also been disclosed in WO 2004/099088.

There is thus a continuing need for water purification systems for treatment of water that is or may be contaminated with chemical, biological and/or radiological contaminants both for normal household purposes as well as for advanced research, industrial and pharmaceutical purposes.

Since contamination or threats of contamination of water are frequently of a highly local character, e.g. on a ship or a in remote village or a camp, there is a need for a fixed or portable water purification system that can be rapidly and easily deployed at a location of actual or potential contamination. Of particular relevance is a system that can effectively remove contaminants from an actually or potentially contaminated water supply, such as sea water, to produce treated water that is suitable for human consumption.

Since the discovery of the aquaporin water transport proteins, which are distinguished by their ability to selectively transport $H_2O$ molecules across biological membranes, there has been a certain interest in devising an artificial water membrane incorporating these proteins, cf. US Patent Application No. 20040049230 "Biomimetic membranes" which aims to describe how water transport proteins are embedded in a membrane to enable water purification. The preferred form described has the form of a conventional filter disk. To fabricate such a disk, a 5 nm thick monolayer of synthetic triblock copolymer and protein is deposited on the surface of a 25 mm commercial ultrafiltration disk using a Langmuir-Blodgett trough. The monolayer on the disk is then cross-linked using UV light to the polymer to increase its durability. The device may be assayed by fitting it in a chamber that forces pressurized source water across the membrane. However, there is no guidance as to how one should select a synthetic triblock copolymer nor is there any data in support of the actual function of the embedded aquaporin.

It has been suggested that a water purification technology could be created by expressing the aquaporin protein into lipid bilayer vesicles and cast these membranes on porous supports, cf. James R. Swartz, home page.

The invention primarily aims at developing an industrial water filtration membrane and device comprising aquaporins incorporated into a membrane capable of purifying water with the highest purity, e.g. 100%. No techniques or filters known today can perform this task.

SUMMARY OF THE INVENTION

The present invention relates in one aspect to a membrane for filtering of water, which membrane utilizes aquaporin water transport proteins that have been reconstituted in lipid vesicles, and transformed into a supported layer to form a water filtering membrane using a method such as the Langmuir-Blodgett method.

Advantages of the water membranes of the invention include efficient desalination of sea-water (97-98% of the earth water is seawater) without the need for desalination chemicals and the provision of transportable desalination filters (a "coffee filter"-like device capable of separating water and salt), efficient water purification for the semi conductor industry, robust household water/drinking water purification, and water purification without use of electricity, for instance in third world countries.

Thus, the invention relates in one aspect to a water membrane comprising a sandwich construction having at least two permeable support layers separated by at least one lipid bilayer comprising functional aquaporin water channels. In this way the permeable or porous support will allow water molecules to penetrate through the support to reach the at least one lipid bilayer deposited between the support layers. The lipid bilayer(s) comprising dispersed functional aquaporin channels will then filtrate only water, or, in case the aquaporin is a GLpF channel, also glycerol, to the opposite porous support layer resulting in a filtrate consisting of pure water. Preferably this filtered water is ultra pure water (UPW), which is highly purified water, low in ions, particles, organic matter and colloids. The water membrane of the invention represents a new generation of reverse osmosis membranes utilizing the most selective water transport channels known.

In the present context, a "water membrane" denotes a structure which allows the passage of water, whereas most other materials or substances are not allowed passage at the same time. Preferred water membranes of the invention a essentially only permeable for water (and in some cases glycerol), whereas solutes and other solvents are not allowed passage.

In a second aspect, the present invention relates to a water membrane comprising a sandwich construction having at least two lipid monolayers, which, when assembled into one bilayer, comprises functional aquaporin water channels, said at least two lipid monolayers being separated by at least one permeable support layer. In this embodiment, the permeable support layer thus separates two lipid monolayers which are capable of forming lipid bilayers when the support layer includes perforations/punctures.

A further aspect of the invention relates to a water filtering device comprising the water membrane of the invention, optionally enclosed in the stabilizing membrane, which has been mounted in a housing having an inlet for aqueous liquid to be purified and an outlet for purified water.

The invention further relates to a method of preparing a water membrane comprising the steps of
a) obtaining lipid micro-vesicles containing aquaporin water channels comprising at least 0.1% mol/mol of said micro-vesicles,
b) fusing said vesicles into a planar lipid bilayer on an essentially planar, permeable support having a hydrophilic surface, wherein the aquaporin protein covers at least 1% of the bilayer area,
c) optionally repeating step b) to obtain multiple fused bilayers,
d) depositing a second essentially planar, permeable support having a hydrophilic surface on the lipid bilayer obtained in step b) or step c) to obtain a sandwich structure, and
e) optionally enclosing the obtained sandwich structure in a permeable stabilizing membrane.

The invention also relates to a method of preparing a water membrane, comprising the steps of
a) obtaining lipid micro-vesicles containing aquaporin water channels comprising at least 0.1% mol/mol of said micro-vesicles,
b) fusing said vesicles into planar lipid bilayers assembled around an essentially planar, permeable support having a hydrophobic surface, wherein the aquaporin protein covers at least 1% of the bilayer area, and
c) optionally enclosing the obtained sandwich structure in a permeable stabilising membrane.

The invention further relates to a reverse osmosis water filtering device comprising, as a reverse osmosis filtering membrane, a water membrane (e.g. a water membrane of the invention) comprising functional aquaporin water channels.

The invention also relates to a water filtering device for extracting and recovering water from body fluids, such as urine, milk and sweat/perspiration, comprising a water membrane comprising functional aquaporin water channels.

In addition, the present invention relates to a method of preparing pure water resulting from filtering a natural or polluted water source through the water membrane of the invention. Said pure water is characterized by the absence of pollutants, such as dissolved substances or particles. The invention furthermore relates to a method of obtaining purified water by filtering a water source using a reverse osmosis membrane comprising functional aquaporin water channels.

Further, a different aspect of the invention relates to a hydrophobic polymer film, which is described in detail below.

Finally, the general design of the water membranes of the present invention is also believed to be applicable to membranes for other purposes, where other transmembrane proteins than aquaporins have been incorporated in membranes otherwise designed as the water membranes of the present invention. Such membranes are also part of the present invention, and such membranes are in all aspects except from the choice of transmembrane protein identical to the membranes disclosed herein, and all disclosures concerning such membranes apply mutatis mutatndis to membranes containing other transmembrane proteins than aquaporins.

Transmembrane proteins different from aquaporins suitable for inclusion in the membranes of the present invention are for instance selected from, but not limited to, any transmembrane protein found in the Transporter Classification Database (TCDB). TCDB is accessible at the TCDB website.

Examples of transmembrane proteins included in the present invention from TCDB are:
Aerolysin channel-forming toxin
Agrobacterial target-host cell-membrane anion channel
a-Hemolysin channel-forming toxin
Alamethicin channel Alginate export porin
Amoebapore
Amphipathic peptide mastoparan
Amyloid b-protein peptide
Animal inward-rectifier K$^+$ channel
Annexin
Apoptosis regulator
ArpQ holin
AS-48
ATP-gated cation channel
Autotransporter
*Bacillus subtilis* j29 holin
Bacterial type III-target cell pore
Bactericidal permeability-increasing protein
Bacteriocin AS-48 cyclic polypeptide
Bacteriorhodopsin
Beticolin channel
BlyA holin
Botulinum and tetanus toxin
*Brucella-Rhizobium* porin
*Campylobacter jejuni* major outer membrane porin
Cathilicidin
cation channel
Cation-channel-forming heat-shock protein 70
Cecropin
Channel-forming *Bacillus* anthrax protective antigen
Channel-forming ceramide
Channel-forming colicin
Channel-forming colicin V
Channel-forming d-endotoxin insecticidal crystal protein
Channel-forming e-toxin
Channel-forming leukocidin cytotoxin
Chlamydial porin
Chloride channel
Chloroplast membrane anion-channel-former
Chloroplast outer-membrane solute channel
Cholesterol-binding, thiol-activated cytolysin
Clostridial cytotoxin
Complement protein C9
Complexed polyhydroxybutyrate-Ca$^{2+}$ channel
Corynebacterial porin
Cph1 holin
C-type natriuretic peptide
Cyanobacterial porin
Cyclodextrin porin
Cytohemolysin
Cytotoxic amylin
Defensin
Dermaseptin
Diphtheria toxin
Divergicin A
Earthworm lysenin toxin
Envelope virus E1 channel
Epithelial chloride channel
Epithelial Na$^+$ channel
FadL outer-membrane protein
Fusobacterial outer-membrane porin
Gap-junction-forming connexin
Gap-junction-forming innexin
General bacterial porin
Glucose-selective OprB porin
Glutamate-gated ion channel of neurotransmitter receptors
gp91$^{Phox}$ phagocyte NADPH-oxidase-associated cyt b$_{558}$ H$^+$-channel
Gramicidin A channel
H$^+$- or Na$^+$-translocating bacterial flagellar motor
H$^+$- or Na$^+$-translocating bacterial MotAB flagellar motor/ExbBD outer-membrane transport
*Helicobacter* outer membrane porin
HP1 holin
Influenza virus matrix-2 channel
Insect defensin
Intracellular chloride channel
j11 holin
jAdh holin
jU53 holin
Lactacin X
Lacticin 481
Lactocin S
Lactococcin 972
Lactococcin A
Lactococcin G
Large-conductance mechanosensitive ion channel
lholin S
Ligand-gated ion channel of neurotransmitter receptors
LrgA holin
LydA holin
Magainin
Major intrinsic protein
Melittin
Metal-ion transporter (channel)
Microcin E492
Mitochondrial and plastid porin
Mycobacterial porin
Nisin
Nonselective cation channel-1
Nonselective cation channel-2
Nucleoside-specific channel-forming outer-membrane porin
OmpA-OmpF porin
OmpG porin
Organellar chloride channel
Outer-bacterial-membrane secretin
Outer-membrane auxiliary protein
Outer-membrane factor
Outer-membrane fimbrial usher porin
Outer-membrane porin
Outer-membrane receptor
P2 holin TM
P21 holin S
Pediocin
Phospholemman
Pilosulin
Plant defensin
Plant plasmodesmata
Plant thionine
Plantaricin EF
Plantaricin JK
Plastid outer-envelope porin of 16 kDa
Plastid outer-envelope porin of 21 kDa
Plastid outer-envelope porin of 24 kDa
Polycystin cation channel
Polyglutamine ion channel
Pore-forming equinatoxin
Pore-forming hemolysin E
Pore-forming RTX toxin
PRD1 holin M
Prion peptide fragment
*Pseudomanas syringae* HrpZ target-host cell-membrane
*Pseudomonas* OprP porin
Raffinose porin
*Rhodobacter* PorCa porin
Ryanodine-inositol-1,4,5-trisphosphate receptor Ca$^{2+}$ channel Saponin channel
Shiga toxin B-chain
Short-chain amide and urea porin
Small-conductance mechanosensitive ion channel
Sugar porin
Syringomycin channel
Syringopeptin channel
T4 holin
T4 Immunity holin
T7 holin
Tachyplesin
Tolaasin channel
TonB-ExbB-ExbD/TolA-TolQ-TolR of energizers for outer-membrane receptor (OMR)-medi-Transient receptor potential $Ca^{2+}$ channel
Tripartite hemolysin BL
Two-partner secretion porin
Type B influenza virus NB channel
Urea transporter (channel)
Urea/amide channel
Vacuolating cytotoxin
*Vibrio* chitoporin/*Neisseria* porin
Voltage-gated ion channel superfamily
Whipworm stichosome porin
Yeast killer toxin K1
Yeast stretch-activated, cation-selective, $Ca^{2+}$ channel Further aspects of the invention include the use of the water membrane to extract excess water from aqueous substances or solutions, e.g. to obtain increased concentration of a desirable solute.

BRIEF DESCRIPTION OF THE DRAWINGS

FIG. 13 is a drawing illustrating the vesicle fusion procedure. Vesicles adsorb to the substrate and rupture to make a supported bilayer.

DETAILED DESCRIPTION OF THE INVENTION

Figure 1:
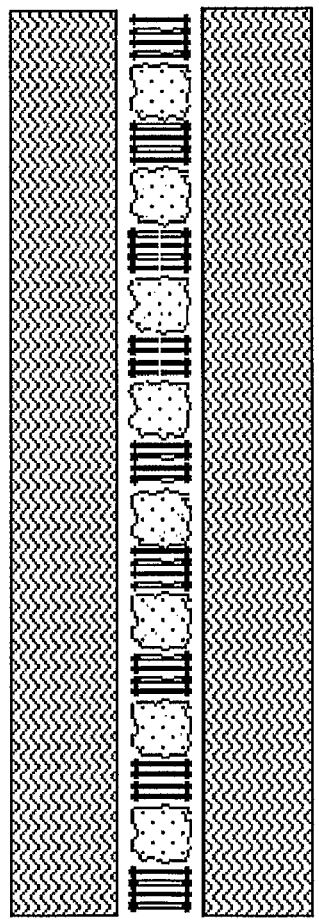
FIG. 1 is a diagram showing various components of a water membrane according to one embodiment of the present invention having supported lipid bilayers with incorporated aquaporin molecules in a sandwich structured example of a water membrane according to the invention.
Figure 1:
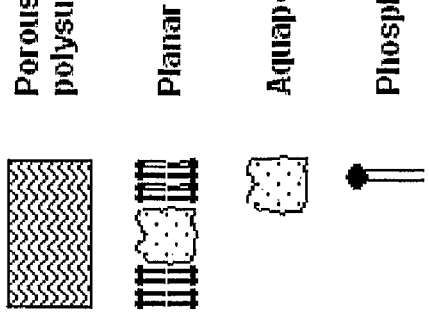
Figure 2:
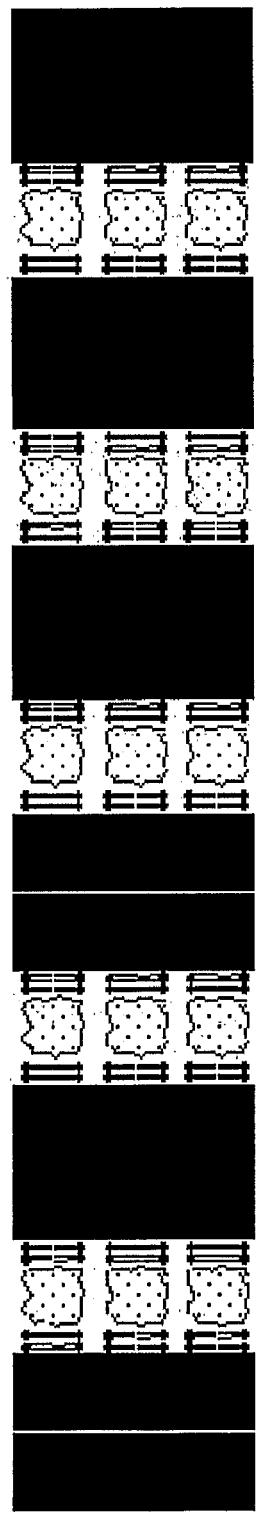
FIG. 2 is a diagram showing various components of a water membrane according to one embodiment of the present invention having supported lipid bilayers with incorporated aquaporin molecules in a sandwich structured example of a water membrane, wherein the lipid bilayers comprising the aquaporin channels is inside the pores of the permeable or porous support material.
Figure 3:
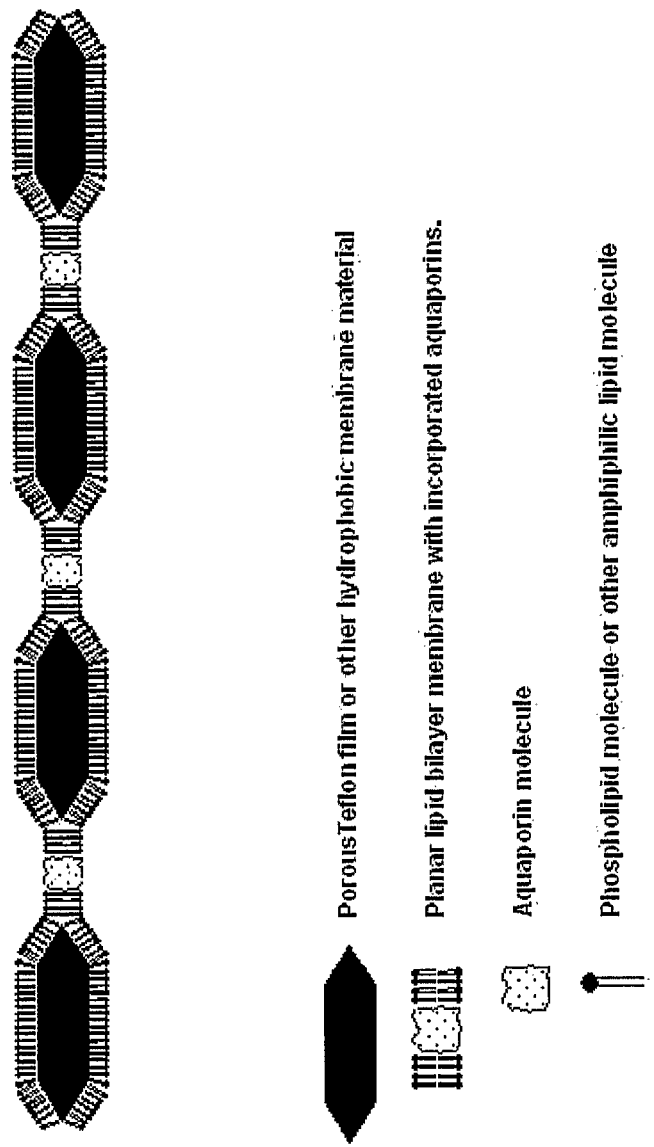
FIG. 3 is a drawing describing the design of a biomimetic membrane comprising aquaporins. The figure shows the various components of the membrane according to another embodiment of the present invention having supported lipid bilayers with incorporated aquaporin molecules sandwiched around a porous teflon film.
Figure 4:
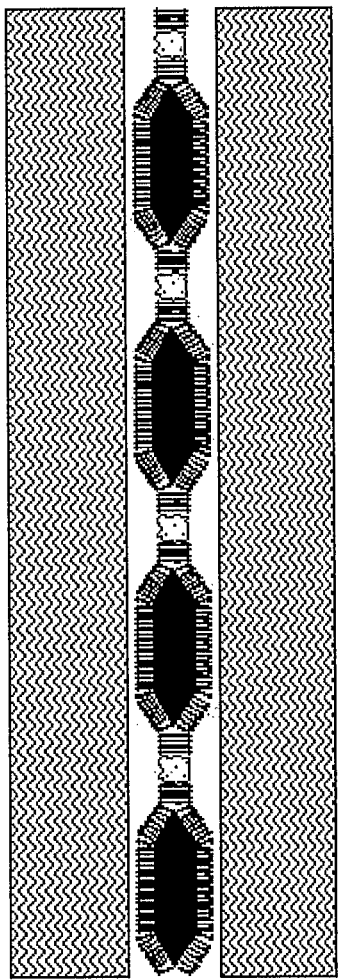
FIG. 4 is a drawing describing the design of a biomimetic membrane comprising aquaporins. The figure shows the various components of the membrane according to another embodiment of the present invention having supported lipid bilayers with incorporated aquaporin molecules sandwiched around a porous teflon film, and further encapsulated in a sandwich construct.
Figure 5:
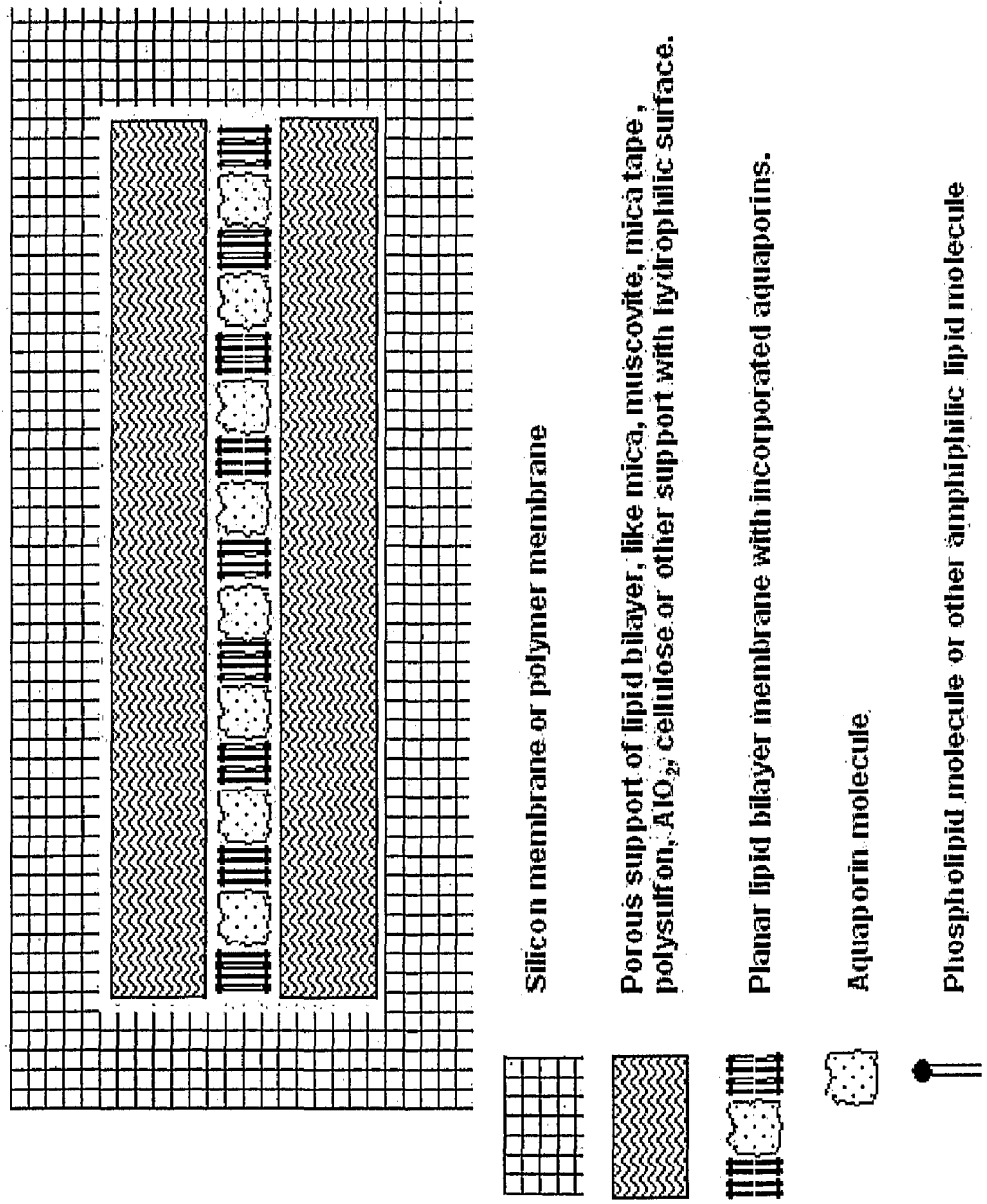
FIG. 5 is a diagram showing various components of a water membrane comprising an encapsulated sandwich structured lipid brayer with incorporated aquaporin molecules.
Figure 6:
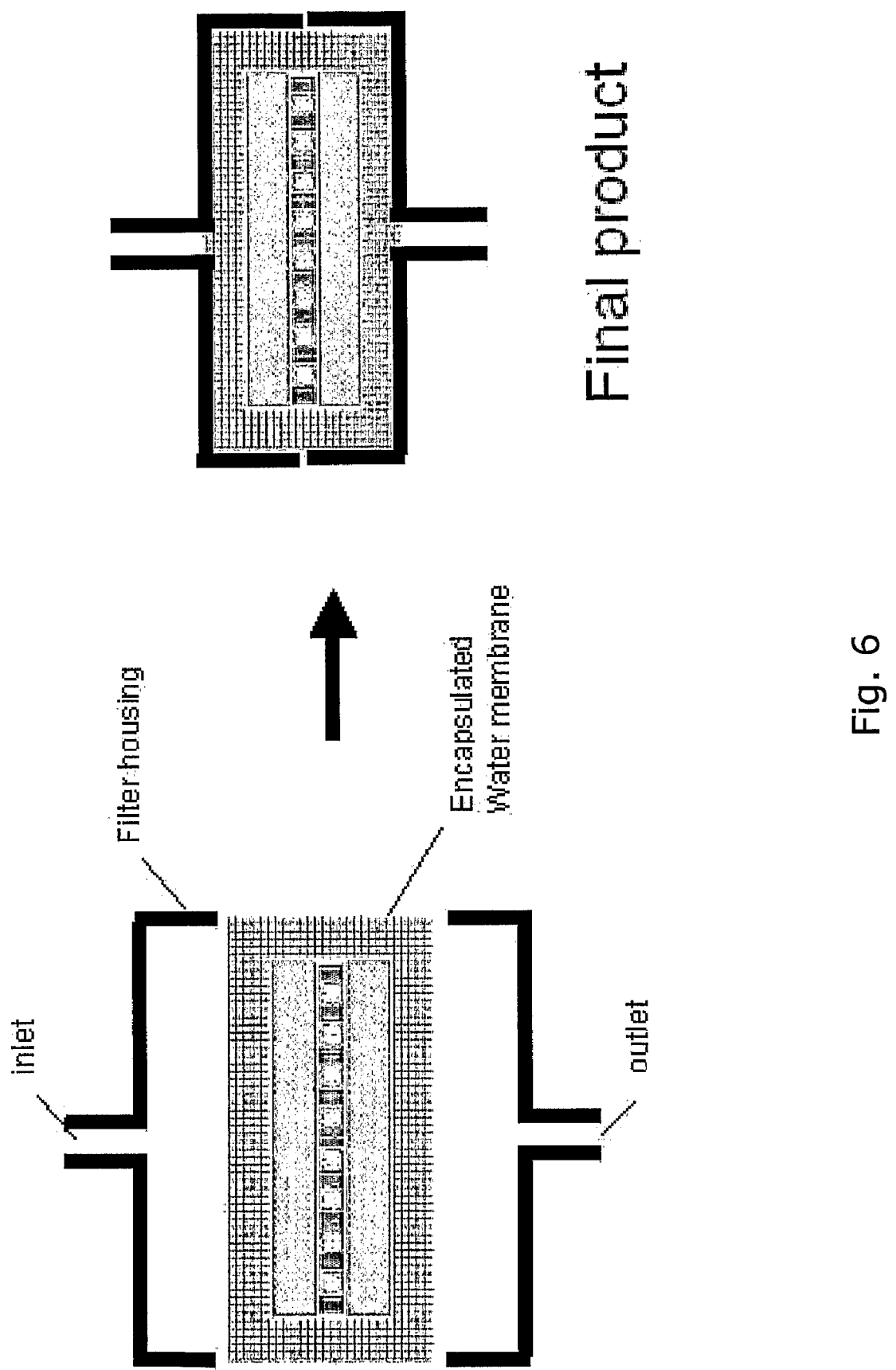
FIG. 6 is an illustration of the encapsulated water membrane of the invention when mounted in a filter housing having an inlet and an outlet according to another embodiment of the present invention.
Figure 7:
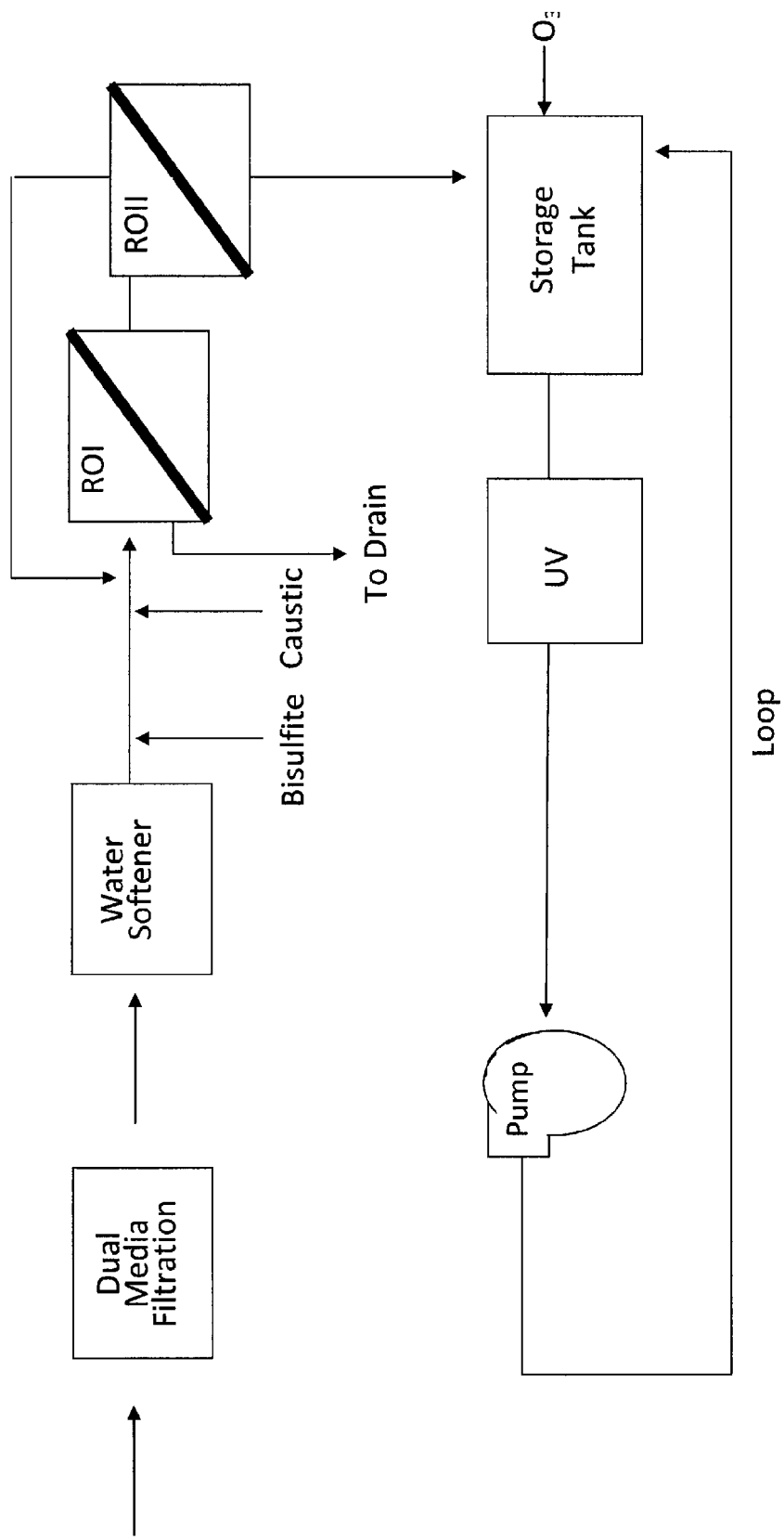
FIG. 7 is a diagram showing various components of a water purification system, according to yet another embodiment of the present invention. The system comprises the components of a crude water inlet, dual media filtration compartment, water softener compartment, optional bisulfite and caustic addition, reverse osmosis filters 1 and 2 (RO1, RO2) connected to a pump with a loop for additional purification through the RO1 and RO2 filters, outlets to drain and storage tank with UV desinfection compartment

Living cells are enclosed by a lipid bilayer membrane, separating the cells from other cells and their extracellular medium. Lipid bilayer membranes are essentially impermeable to water, ions, and other polar molecules; yet, in many instances, such entities need to be rapidly and selectively transported across a membrane, often in response to an extra- or intracellular signal. The water-transporting task is accomplished by aquaporin water channel proteins (Preston et al., 1992). Aquaporins are crucial for life in any form and they are found in all organisms, from bacteria via plants to man. Aquaporins facilitate rapid, highly selective water transport, thus allowing the cell to regulate its volume and internal osmotic pressure according to hydrostatic and/or osmotic pressure differences across the cell membrane. The physiological importance of the aquaporin in humans is perhaps most conspicuous in the kidney, where ~150-200 liters of water need to be reabsorbed from the primary urine each day, that is, aquaporin facilitated water transport is invoked when water rapidly must be retrieved from a body fluid. In kidneys, this is made possible mainly by two aquaporins denoted AQP1 and AQP2 (11 different aquaporins are known in humans). In plants, aquaporins are also critical for water absorption in the root and for maintaining the water balance throughout the plant (Agre et al., 1998, Borgnia et al., 1999). Studies of water transport in various organisms and tissues suggested that aquaporins have a narrow pore preventing any large molecule, ions (salts) and even proton ($H_3O+$) and hydroxyl ion (OH−) flow while maintaining an extremely high water permeation rate; ~$10^9$ molecules H2O per channel per second (Agre et al., 1998, Borgnia et al., 1999). Until 2000 and 2001 where the first high-resolution 3D structure of AQP1 and that of the related glycerol-conducting bacterial channel protein aquaglyceroporin GlpF were reported (Fu et al., 2000; Murata et al., 2000; Ren et al., 2001; Sui et al., 2001), little was known about the origin of water selectivity.

However, based on the experimental structures, detailed computer models were put forward explaining not only the high permeation rate and the strict water selectivity but also the ability of aquaporins to prevent proton leakage (de Groot and Grubmülller, 2001; Tajkhorshid et al., 2002, Jensen et al., 2003, Zhu et al. 2003, de Groot et al., 2003, Burykin and Warshel 2003, Ilan et al., 2004, Chakrabarti at al., 2004). In essence, the architecture of the aquaporin channel allows water molecules to pass only in a single file while electrostatic tuning of the channel interior controls aquaporin selectivity against any charged species, that is, transport of any salt (ion) as well as protons and hydroxyl ions is abrogated (de Groot and Grubmüller, 2001; Tajkhorshid et al., 2002, Jensen et al., 2003, Zhu et al. 2003, de Groot et al., 2003, Burykin and Warshel 2003, Ilan et al., 2004, Chakrabarti at al., 2004). In short, this implies that only water molecules pass through the aquaporin water pore, nothing else.

Each unit in an aquaporin channel transports ~$10^9$ $H_2O$ molecules/sec, i.e., ~$4 \times 10^9$ molecules/channel/sec. Hence, 1 g of aquaporin is capable of transporting ~720 liter of water/sec at very high pressure. The resulting water filtrated through a functional aquaporin channel is ~100% purified water, absent of ions, particles, organic matter and colloids, e.g. consisting of ~100% $H_2O$.

Figure 8:
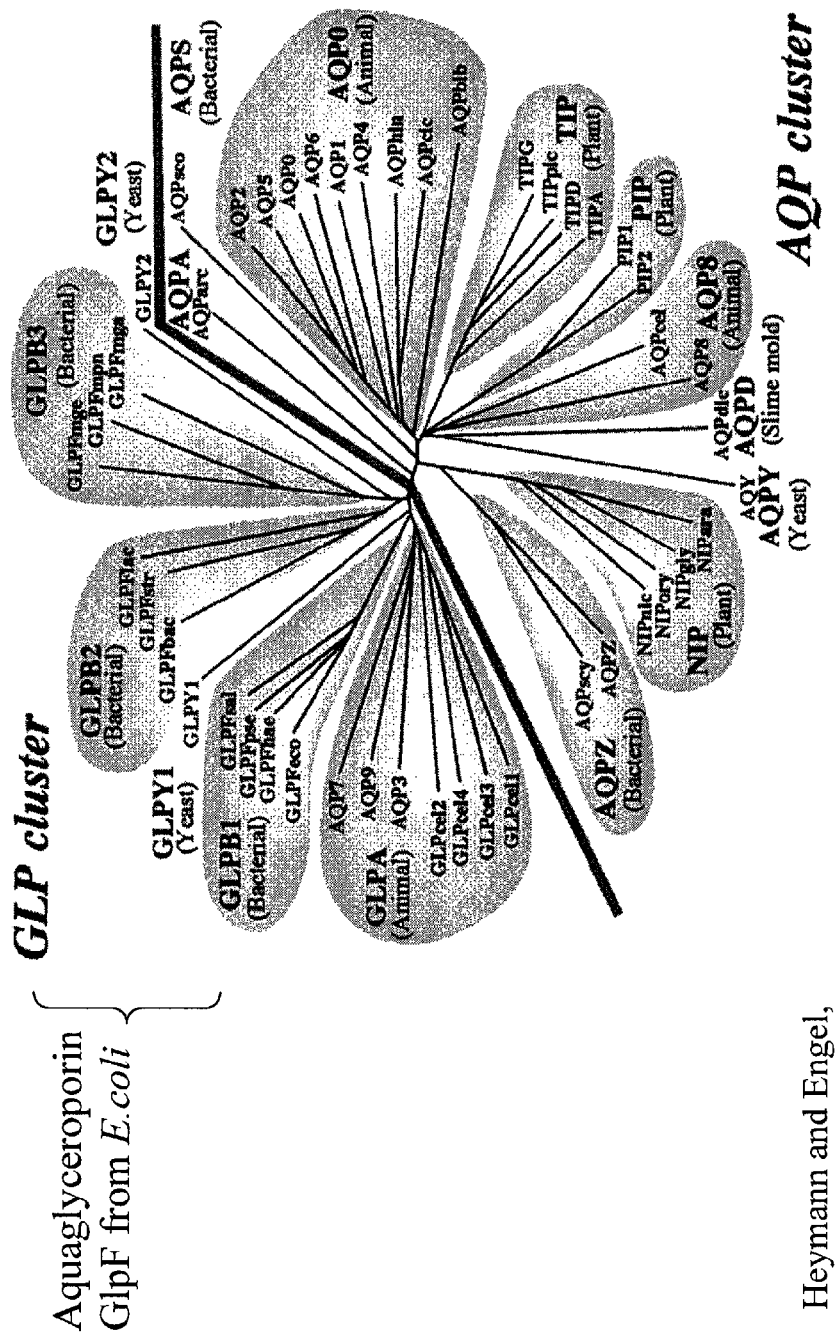
FIG. 8 illustrates the various members of the aquaporin and aquaglyceroporin group of proteins.

The aquaporin family of membrane proteins as used herein include also the GLpF proteins which in addition to water molecules also channels glycerol. A preferred aquaporin is of plant origin, such as a Tonoplast Intrinsic Protein (TIP), a Plasma Membrane Intrinsic Protein (PIP), or a Nodulin-26 like Intrinsic Protein (NIP) aquaporin, cf. FIG. 8.

The membranes of the invention disclosed below will only pass water, thus facilitating water purification, desalinization, and molecular concentration through reverse osmosis. The aquaporins are known to exclude the passage of all contaminants, including bacteria, viruses, minerals, proteins, DNA, salts, detergents, dissolved gases, and even protons from an aqueous solution, but aquaporin molecules are able to transport water because of their structure. The related family of aquaglyceroporins (GLPF) are in addition able to transport glycerol. Every aquaporin comprises transmembrane alpha-helical domains that anchor the protein in a membrane and two highly conserved NPA (Asn-Pro-Ala) loops that come together apex to apex in the center of the protein to form a kind of hourglass shape. It has been shown that water movement is symmetrical and can proceed in either direction; this fact is important because this process does not consume energy. Water moves through the membrane in a particular direction because of hydraulic or osmotic pressure.

Accordingly, purified water can be obtained from undrinkable sources or, if the source water contains chemicals of interest, the water can be selectively removed, leaving a high concentration of the wanted chemicals in the input chamber. Importantly, however, the aquaporins are also suited to this invention for reasons other than their exclusive selectivity for water. Many members of this protein family are able to withstand the harsh conditions of contaminated source water without losing function. Aquaporins resist denaturing or unraveling from exposure to acids, voltages, detergents, and heat. Therefore, the membrane of the invention can be used to purify source water contaminated with materials that might foul or destroy other membranes, and it can be used in areas that experience consistently high temperatures.

Aquaporins are also mutable. Since the proteins may be specifically expressed in host bacteria according to a genetic sequence that influences its final shape and function, a technician can easily change its genetic code in order to change the protein's characteristics. Therefore the protein can be engineered to fulfill a desired application that may be different from the protein's original function. For example, by simply changing a particular amino acid residue near the center of the water channel to cysteine, the Aquaporins produced would bind any free mercury in the solution and cease transporting water due to the blockage. Thus, these mutant proteins used in a membrane device could detect mercury contamination in a water sample by simply ceasing flow when the concentration of the toxic substance rises too high.

Lastly, new protein-based membranes are also very inexpensive to produce. Lipid micro vesicles comprising cell membrane fractions with AQP1 derived from bovine red blood cells are a cheap source of aquaporin.

Alternatively, aquaporin may be harvested in milligram quantities from an engineered *E. coli* bacterial strain. It is estimated that about 2.5 mg of pure protein can be obtained from each liter of culture that is producing it, cf. US Patent Application No. 20040049230.

Thus, we herein disclose methods and apparatus utilizing biological components to achieve the highly efficient production of completely pure water from fouled, salty, or otherwise contaminated water. The invention demonstrates the integration of water transporting biological proteins with an external device, and points the way toward a manufacturing pathway capable of large-scale production of water purification devices.

$1^{st}$ Aspect of the Invention

In the above-described first aspect of the invention, the water membrane comprises a sandwich construction having at least two permeable support layers separated by at least one lipid bilayer comprising functional aquaporin water channels The water membrane of the first aspect of the invention thus consists of an amphiphilic lipid membrane, such as a membrane comprising lipids described in Table 1. Thus, the lipid bilayer(s) essentially consist(s) of amphiphilic lipids selected from the group consisting of phospholipids, phosphoglycerides, sphingolipids, and cardiolipin, as well as mixtures thereof, e.g. phospholipids such as 1,2-dipalmitoyl-sn-phosphatidylcholine (DPPC), or mixtures of phospholipids.

Alternatively, the lipid bilayers may consist essentially of or contain polymerizable lipids, cf. Table 1.

The water membrane of the invention thus comprises reconstituted aquaporin water channels on a porous support. Useful support materials with a hydrophilic surface for the preparation of water membranes according to the invention is preferably selected from mica such as muscovite, mica tape, polysulfon, $AlO_2$, and polymeric materials having a hydrophilic surface, e.g. cellulose. The support materials are essentially planar which means that the support is preferably planar, but curvature of the support is allowable, such as needed when spirally wound filters are manufactured. In this case the support material is preferably flexible, such as cellulose membranes.

The porous support may preferably comprise a material such as mica having an essentially planar structure with a hydrophilic surface and wherein micro or nano pores have been formed, e.g. by etching. Hence, in an embodiment of the first aspect, the permeable support layer comprises an essentially planar, hydrophilic layer comprising mica or mica tape having a layer thickness in the mm to pm scale and wherein nanopores having a diameter of less than approximately 50 nm (typically in the 10-40 nm range) have been formed (e.g. by etching such as by a track-etch technique). The mica is preferably muscovite. The permeable support layers may also comprise a hydrophilized membrane surface, such as a membrane selected from the group consisting of silicone membranes, polysulfon, $AlO_2$, and polymers such as cellulose having a hydrophilic surface, wherein nanopores having a diameter of less than approximately 50 nm (typically in the 10-40 nm range) have been formed.

The lipid membrane comprising aquaporin channels may be a bilayer resembling the natural constitution of biological cell membranes, or the lipid membrane may consist of multiple bilayers of fused deposited lipid vesicles. The lipids are preferably of amphiphilic nature, such as the phospholipids (or phosphoglycerides), sphingolipids and cardiolipin. When depositing the lipid layers on the porous substrate, the aquaporin channels may preferably be deposited adjacent to or in the preexisting pores in the support material.

The permeable or porous support used in preferred embodiments of the invention is preferably prepared according to R. M. Webber, J. L. Anderson, M. S. John, Macromolecules 23 (1990), 1026-1034, wherein it is described that:

"The membranes were made from thin sheets of muscovite mica, approximately 7 nm thick, by a track-etch technique. With track-etched membranes, pores are created by etching the tracks created by collimated fission fragments from a Californium 252 source with a hydrofluoric acid solution. The number of pores (n) is controlled by the exposure time of the membrane to the fission source, while the pore radius is determined by the etching time, temperature, and concentration of the aqueous hydrofluoric acid bath. The pores are uniform in size and perpendicular to the membrane surface. The uniformity of pore size is an important feature of these membranes because a significant pore-size distribution would lead to ambiguous results for the hydrodynamic thickness of the polymer layer due to biased flow through the larger pores. The pore cross-sectional area fraction for the irradiated part of the membranes was approximately 1%; therefore, the total number of single pores, as modeled by a binomial pore-size distribution, was greater than 96%. The pore length (1) equaled the membrane thickness, since the pores were perpendicular to the membrane face; the thickness was determined from the known dimensions and weight of the membrane."

It is preferred to obtain a final number and distribution of pores which approximately equals the number and distribution of aquaporin channels in the lipid layer.

$2^{nd}$ Aspect of the Invention

It is also possible to reconstitute aquaporin water channels in a planar lipid brayer assembled around a porous support membrane with a hydrophobic surface, such as teflon film, where lipid monolayers assemble on each side of the porous support membrane. In the pores of the porous support membrane lipid bilayers will assemble, where aquaporin water channels can be reconstituted.

The second aspect of the invention is thus constituted by a water membrane comprising a sandwich construction having at least two lipid monolayers, which, when assembled into one bilayer, comprises functional aquaporin water channels, said at least two lipid monolayers being separated by at least one permeable support layer. Typically, the support layer comprises a hydrophobic perforated material which forms the contact surface with the lipid monolayers and wherein the lipid bilayer is formed in the perforations of the hydrophobic perforated material.

It is preferred that the hydrophobic material has a degree of hydrophobicity corresponding to a contact angle of at least 100° between a droplet of deionized water and the hydrophobic material, where the contact angle measurement is performed at 20° C. and atmospheric pressure, but higher degrees of hydrophobicity are preferred, such as those corresponding to contact angles of at least 105°, 110°, 120° and 120°. Preferred hydrophobic materials are parafilm or Teflon.

The hydrophobic material is typically planar (but may be flexible and thus curved) and the perforations are typically evenly distributed and substantially all of substantially the same geometric shape in the intermediate plane between the 2 surfaces of the hydrophobic material; details pertaining to the perforations in the hydrophobic material are provided below.

The "intermediate plane" is defined as the plane consisting of points from which the perpendicular distance to either both of the 2 surfaces of the planar hydrophobic material is the same.

The size of the perforations in the hydrophobic material should merely ensure that stable bilayers of amphiphilic lipids can be formed in the perforations, so they may have sizes in the nm, µm or mm range.

The hydrophobic material is preferably perforated in such a way that the ratio between perforation are and non-perforated area of the material is maximized, since this provides a maximum area of lipid bilayer with aquaporins to effect water transport. The pattern constituted by the perforations is thus of importance as is the distance between each perforation. An optimum pattern is a hexagonal arrangement of the perforations with a minimum "wall thickness" between each perforation in the pattern. However, at quadratic pattern may also prove sufficient.

The water membrane of the second aspect of the invention hence also comprises of an amphiphilic lipid membrane, such as a membrane comprising lipids described in Table 1. Thus, the lipid bilayer(s) essentially consist(s) of amphiphilic lipids selected from the group consisting of phospholipids, phosphoglycerides, sphingolipids, and cardiolipin, as well as mixtures thereof, e.g. phospholipids such as 1,2-dipalmitoyl-sn-phosphatidylcholine (DPPC), or mixtures of phospholipids. The difference from the first aspect is primarily that the membrane only constitutes a bilayer in areas where the hydrophobic support is perforated, whereas the lipids are organised with their hydrophobic ends facing the hydrophobic support and the hydrophilic ends facing the aqueous environment.

Preparation of Bilayers

Figure 12:
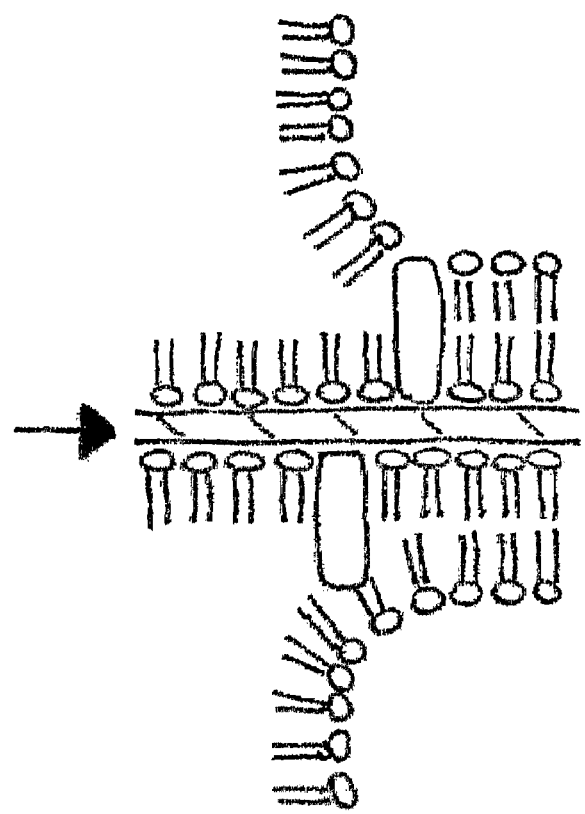
FIG. 12 is a drawing illustrating the preparation of supported bilayers by Langmuir-Blodgett deposition of lipids from the air-water interface. Deposition of the first monolayer is shown to the left and of the second layer to the right.
Figure 12:
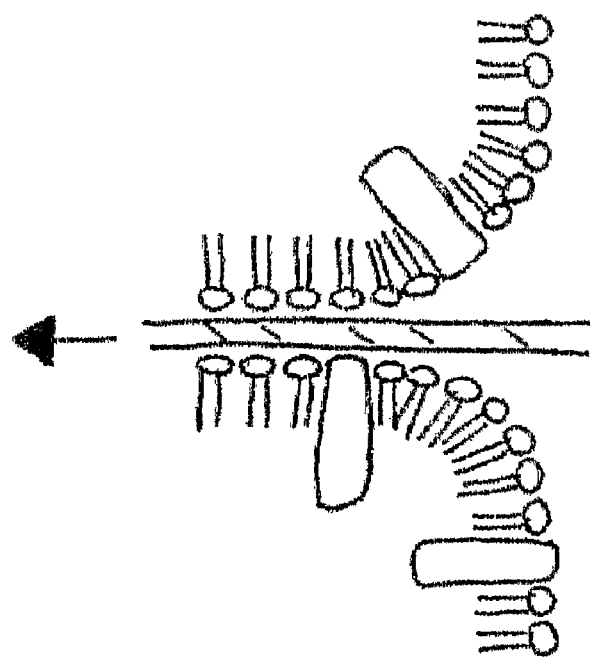

Intrinsic permeability of the membrane material must be secured. A material with low permeability is to be preferred, however, it must at the same time be robust and able to incorporate aquaporins to constitute overall a stable and dense 2D filtering array. Various procedures are commonly used for preparing supported lipid bilayers. A simple technique is the Langmuir-Blodgett method. A solution of lipid in a suitable organic solvent is spread on an aqueous sub phase in a Langmuir trough and the organic solvent is evaporated. A pair of movable barriers is used to compress the lipid film laterally to a desired surface pressure. Then the substrate is passed vertically through the film thereby transferring a one molecule thick lipid layer (monolayer) onto the substrate (see FIG. 12). A second monolayer can be transferred by passing the substrate through the film once more. A total of three mono layers have been transferred by the vertical (Langmuir-Blodgett) deposition method, however, a fourth layer may be transferred by using horizontal, the so called Langmuir-Schaeffer (LS), deposition for the last layer. The methods can be used with a variety of lipids. Native biological membranes often are asymmetric. Both LB and LS offer the possibility of preparing asymmetric bilayers. This is done by exchanging the lipid film on the sub phase between depositions.

Another way of preparing supported bilayers is the vesicle fusion method (Brian and McConnell 1984). A solution of small unilamellar vesicles (SUVs) is applied onto the surface of a piece of hydrophilized silicon or freshly cleaved mica.

When this sample is left at low temperature (4° C.) the vesicles fuse with the surface to make a continuous bilayer (FIG. 13). Without being bound to any theory it has been hypothesized that the vesicles first adsorb to the surface of the substrate then fuse to make a flat, pancake-like structure and finally rupture and spread out resulting in a single bilayer on the surface (Reviakine and Brisson 2000). It has also been suggested that after fusion with the substrate only the part of the vesicle which is in direct contact with the substrate becomes the supported bilayer (Leonenko et al. 2000). With this mechanism the vesicle ruptures at the edges with the highest curvature and the top part of the bilayer may then migrate to the surface of the substrate to increase the size of the formed supported bilayer. It has been reported that bilayers are formed within minutes of applicating the solution onto the substrate (Tokumasu et al. 2003) but this short incubation time may result in incomplete bilayers. Hours or overnight incubation have also been reported (Reimhult et al. 2003, Rinia et al. 2000).

Figure 14:
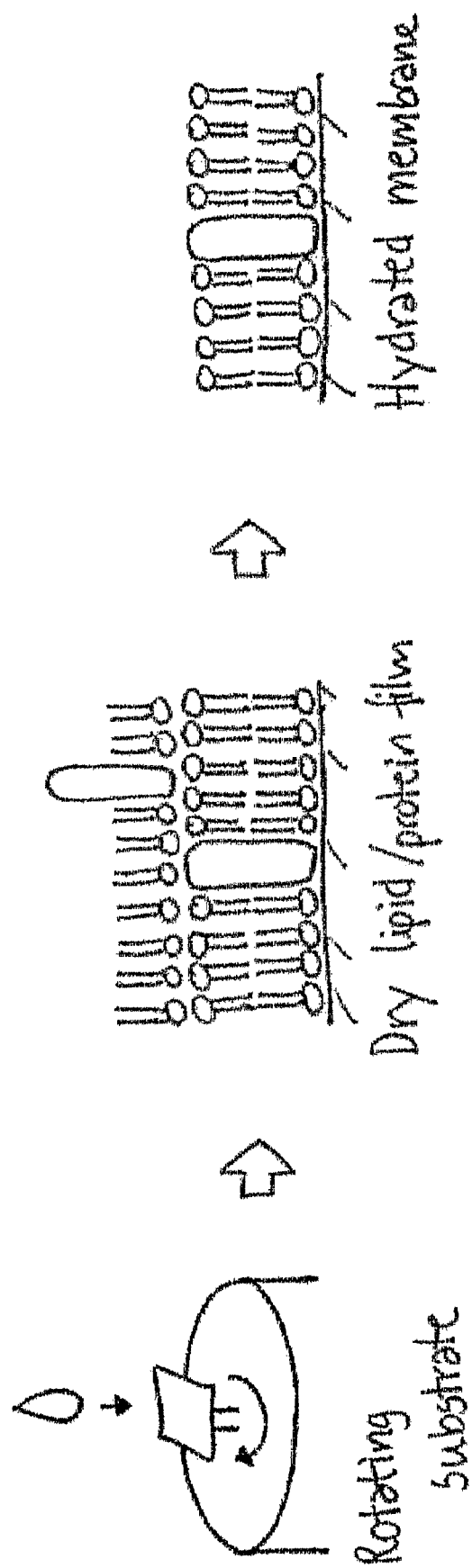
FIG. 14 is a drawing illustrating supported lipid bilayer preparation by spin-coating.

A third technique which can be used to prepare supported bilayers is spin-coating (Reimhult et al. 2003, Simonsen and Bagatolli 2004). In spin-coating the lipid is dissolved in a suitable solvent and a droplet is placed on the substrate which is then rotated while the solvent evaporates and a lipid coating is produced. Depending on the concentration of the lipid solution the spin-coated film consist of one or more lipid bilayers. However, upon hydration the multiple layers have been shown to be unstable, and usually only one supported brayer remains on the surface (FIG. 14). This procedure is easy and fast and it has been done with low-melting lipids (POPC) as well as lipids with intermediate (DPPC) and very high transition temperature (ceramide). Useful lipids include, e.g., phospholipids and amphiphilic lipds.

When one further wants to incorporate peptides and proteins in the supported bilayers the vesicle fusion technique is the most applicable, since the other procedures mentioned involve solubilization of the proteins or peptides in organic solvents. Many membrane proteins may denature in organic solvents especially if they contain large domains exposed to the aqueous solution on either side of the membrane. It is therefore preferred to inset the peptide or proteins in vesicles. Many peptides and proteins such as aquaporins can be co-solubilized with lipid in the organic solvent prior to formation of vesicles and the peptide containing vesicles are then applied to the substrate. This has been done with a number of peptides, for example WALP (Rinia et al. 2000), gramicidin (Mou et al. 1996), clavanin A (van Kan et al. 2003) and Amyloid β Protein (Lin et al. 2001). Membrane proteins such as aquaporins are preferably inserted into vesicles by other means. This can be done using the strategies for reconstitution of membrane proteins into vesicles as described for cytochrome c oxidase as a model protein in the introduction to chapter 4 on pages 41-45 of the thesis "Supported bilayers as models of biological membranes" by Danielle Keller, February 2005, MEMPHYS-center for biomembrane physics, Physics Department, University of Southern Denmark and Danish Polymer Centre, Risø National Laboratory, Denmark.

Multi layer stacking of the individual 2D-arrays are possible and may be desirable. The final dimensions of the stacked arrays will depend on overall robustness and on intrinsic permeability of the chosen membrane material/membrane composition. Stacking might depart from a system where proteins trivially are embedded in a single, probably supported, lipid bilayer. A subsequent series of collapsing vesicles events on the supported bilayer could then provide multi layer filtering unit-devices, given that the vesicles pre-requisite are reconstituted with an appropriate aquaporin. Incorporation of the stacked unit-device into a stabilising membrane or stabilising polymer matrix and subsequent stitching of these individual units would yield an overall filtering mesh, eventually via self-assembly processes.

Common Features of the Aspects of the Invention

A number of features are in common for the various aspects of the invention:

Useful aquaporins for the preparation of water membranes according to the invention are: AQP1, TIP, PIP, NIP, cf. FIG. 8, and mixtures and hybrids thereof. The aquaporins of plant origin are especially desirable, since the risk of including contaminants, such as pathogenic viruses and prions, that are harmful to humans is greatly reduced. In addition, the plant aquaporins are natural gene products of plants and can be overexpressed and produced in plants.

The aquaporin water channel is thus preferably selected from the group consisting of aquaglyceroporins (GLpF), such as a GLPA channel, a GLPB1 channel, a GLPB2 channel, a GLPB3 channel, and a GLPY2 channel, and mixtures and hybrids thereof.

The water membranes of the invention are preferably enclosed in a stabilizing permeable or porous membrane which may be rigid or flexible and which may serve as protection of the water membrane as well as a pre-filter to exclude coarse particulate matter from the aqueous liquid to be purified. Alternatively or additionally, the water membrane of the invention may be deposited on a filter disk to create a water filter.

Useful materials for the stabilizing membrane optionally used to enclose the water membranes of the invention are micro-porous silicone membranes having a relatively small pore size and solidigying at about room temperature or at a temperature below about 50° C.

Useful lipids for reconstitution of aquaporins and formation of lipid bilayers are: POPC, DPPC, ceramide, cf. Table 1 and mixtures hereof.

Table 1 is a list of useful lipids for the formation of lipid bilayers to be used in the water membranes of the invention:

Phosphatidylcholines:
1,2-dimyristoylphosphatidylcholine (DMPC)
1,2-dipalmitoylphosphatidylcholine (DPPC)
1,2-distearoylphosphatidylcholine (DSPC)
1,2-dioleoylphosphatidylcholine (DOPC)
1,2-dimyristoleoylphosphatidylcholine
1,2-dipalmitoleoylphosphatidylcholine
1,2-dipetroselinoylphosphatidylcholine
1,2-dielaidoylphosphatidylcholine
1,2-dilinoleoylphosphatidylcholine
1,2-dilinolenoylphosphatidylcholine
1,2-dieicosenoylphosphatidylcholine
1,2-diarachidonoylphosphatidylcholine
1,2-dierucoylphosphatidylcholine
1,2-dnervonoylphosphatidylcholine
1-palmitoyl-2-oleoylphosphatidylcholine (POPC)
1-palmitoyl-2-linoleoylphosphatidylcholine
1-palmitoyl-2-arachidonoylphosphatidylcholine
1-palmitoyl-2-docosahexaenoylphosphatidylcholine
1-stearoyl-2-oleoylphosphatidylcholine (SOPC)
1-stearoyl-2-linoleoylphosphatidylcholine
1-stearoyl-2-arachidonoylphosphatidylcholine
1-stearoyl-2-docosahexaenoylphosphatidylcholine
1-oleoyl-2-palmitoylphosphatidylcholine
1-oleoyl-2-stearoylphosphatidylcholine
1,2-didocosahexaenoylphosphatidylcholine Phosphatidylethanolamines:
1,2-dimyristoylphosphatidylethanolamine (DMPE)
1,2-dipalmitoylphosphatidylethanolamine (DPPE)
1,2-distearoylphosphatidylethanolamine (DSPE)
1,2-dioleoylphosphatidylethanolamine (DOPE)
1-palmitoyl-2-oleoylphosphatidylethanolamine (POPE)
1-palmitoyl-2-linoleoylphosphatidylethanolamine
1-palmitoyl-2-arachidonoylphosphatidylethanolamine
1-palmitoyl-2-docosahexaenoylphosphatidylethanolamine
1-stearoyl-2-oleoylphosphatidylethanolamine (SOPE)
1-stearoyl-2-linoleoylphosphatidylethanolamine
1-stearoyl-2-arachidonoylphosphatidylethanolamine
1-stearoyl-2-docosahexaenoylphosphatidylethanolamine
1,2-dielaidoylphosphatidylethanolamine
1,2-dilinoleoylphosphatidylethanolamine
1,2-dilinolenoylphosphatidylethanolamine
1,2-diarachidonoylphosphatidylethanolamine
1,2-didocosahexaenoylphosphatidylethanolamine
1,2-dipalmitoleoylphosphatidylethanolamine Phosphatidylglycerols:
1,2-dimyristoylphosphatidylglycerol (DMPG)
1,2-dipalmitoylphosphatidylglycerol (DPPG)
1,2-distearoylphosphatidylg lycerol (DSPG)
1,2-dioleoylphosphatidylglycerol (DOPG)
1-palmitoyl-2-oleoylphosphatidylglycerol (POPG)
1-palmitoyl-2-linoleoylphosphatidylglycerol
1-palmitoyl-2-arachidonoylphosphatidylglycerol
1-palmitoyl-2-docosahexaenoylphosphatidylglycerol
1-stearoyl-2-oleoylphosphatidylglycerol (SOPG)
1-stearoyl-2-linoleoylphosphatidylglycerol
1-stearoyl-2-arachidonoylphosphatidylglycerol
1-stearoyl-2-docosahexaenoylphosphatidylglycerol Phosphatidylserines:
1-palmitoyl-2-oleoylphosphatidylserine (POPS)
1-palmitoyl-2-linoleoylphosphatidylserine
1-palmitoyl-2-arachidonoylphosphatidylserine
1-palmitoyl-2-docosahexaenoylphosphatidylserine
1-stearoyl-2-oleoylphosphatidylserine (SOPS)
1-stearoyl-2-linoleoylphosphatidylserine
1-stearoyl-2-arachidonoylphosphatidylserine
1-stearoyl-2-docosahexaenoylphosphatidylserine
1,2-dimyristoylphosphatidyiserine (DMPS)
1,2-dipalmitoylphosphatidylserine (DPPS)
1,2-distearoylphosphatidylserine (DSPS)
1,2-dioleoylphosphatidylserine (DOPS)
1,2-didocosahexaenoylphosphatidylserine
1,2-dierucoylphosphatidylserine Special lipids:
Cardiolipin
Bipolar lipids
Natural lipid extracts:
Egg yolk phosphatidylcholine
Bovine heart phosphatidylcholine
Brain phosphatidylcholine
Bovine liver phosphatidylcholine
Soybean phosphatidylcholine
E. Coli phosphatidylethanolamine
Bovine Heart phosphatidylethanolamine
Brain phosphatidylethanolamine
Bovine Liver phosphatidylethanolamine
Egg phosphatidylethanolamine
Bovine liver phosphatidylinositol
Soybean phosphatidylinositol
Brain phosphatidylserine
Soy phosphatidylserine Polymerizable lipids:
1,2-di-10,12-tricosadiynoyl-sn-glycero-3-phosphocholine (DTPC)
1,2-di-10,12-tricosadiynoyl-sn-glycero-3-phosphoethanolamine (DTPE)
1-palmitoyl-2,10,12-tricosadiynoyl-sn-glycero-3-phosphoethanolamine (PTPE)
(DC8,9PC [1,2-bis( 10,12-tricosadiynoyl)-sn-glycero-3-phosphocholine]
diPhyPC [1,2-diphytanoyl-sn-glycero-3-phosphocholine]

Water Treatment Systems and Water Filtering Devices

In one embodiment the invention has the form of a conventional filter disk because it is easily assayed for functionality. To fabricate such a disk, a brayer of phospholipid membrane comprising functional aquaporin protein is deposited on the surface of a 25 mm commercial ultrafiltration disk using a Langmuir-Blodgett trough. In a preferred embodiment of the invention the water membrane is spirally wound optionally together with conventional membranes to form a spiral wound RO module, cf. FIGS. 10. & 11.

The filter disk is mounted in a closed chamber having an inlet and an outlet, such as a filter disk chamber connected through a tube to a water source having a pump that forces pressurized source water across the membrane and out through the outlet. The device is considered functional when only pure water comes through the other side of the membrane and contaminating solutes remain concentrated in the originating chamber. The contaminated solution must be pressurized in order to overcome the natural tendency of pure water to flow into the compartment of the chamber which has the higher number of dissolved particles, thus overcoming the osmotic pressure of the water which is about 10 psi for potable water. It is the purpose of the water membrane of the invention to reverse osmosis and separate the pure water from contaminating solutes. This tendency, or osmotic pressure, of the system can be expressed in pounds per square inch (psi). For example, the osmotic pressure of sea-water is in the range of 360 to 400 psi.

There are several methods that can be used to allow the device to tolerate these types of pressures. One method is to add a high concentration of a non-toxic and easily removable solute to the freshwater chamber to encourage regular osmosis across the membrane while reverse osmosis is also occurring due to chamber pressurization. Also, the pressure required for reverse osmosis can be reduced by using multiple aquaporin membranes in a cascade of sealed, connected chambers containing successively smaller concentrations of contaminants. The resulting pressure required to purify water in each pair of chambers is a fraction of the total pressure necessary for reverse osmosis. Therefore, each membrane only has to withstand a small pressure and has a greater chance of remaining intact. So, if the difference in concentration between each pair of chambers was only 10% instead of 100%, just 10% of the high pressure mentioned above would be needed to purify the source water at each junction. Pure water would be continuously produced in the final chamber with constant pressure and flow.

The aquaporin reverse osmosis membrane can purify water possessing several different types of contamination in only a single step. Traditional high purity systems, require several components that can include a water softener, carbon filters, ion exchangers, UV or chemical sterilization, and a two pass reverse osmosis filter set to be used in conjunction before purified water can be produced. This elaborate set-up cannot remove dissolved gases or substances smaller than 150 Daltons from the source water like the aquaporin membrane can.

Furthermore, all these components require maintenance. UV bulbs require replacement and energy. Ion exchangers need to be chemically regenerated when they are full. Softeners require salt. Carbon and reverse osmosis cartridges must be replaced when they become fouled. Finally, a single step device would require much less space and weigh far less than a typical purification system, and this advantage is enabled by devices comprising the aquaporin water membrane of the invention to be portable.

Aquaporin membranes are also faster than conventional systems. A conventional high-speed reverse osmosis unit can produce about 28.4 liters (7.5 gallons) of clean water per minute. Current research shows the movement of water molecules across an aquaporin saturated lipid membrane (0.0177 mm$^2$) at the rate of 54 µmol/sec. (Pohl, P., Saparov, S. M., Borgnia, M. J., and Agre, P., (2001), Proceedings of the National Academy of Sciences 98, p. 9624-9629). Thus, a theoretical aquaporin reverse osmosis membrane with a surface area of 1.0 m$^2$ could filter up to 3295 liters of pure water per minute. That rate is over 116 times faster than a normal purifier.

The present invention in a still further aspect relates to a system for treatment of water to remove chemical, radiological, biological, and/or particle contaminants therefrom, such system comprising a unitary housing having an inlet arranged for connection to an external water source, wherein the unitary housing has disposed therein one or more water filtering units comprising a water membrane of the invention arranged to treat water from the external water source to produce an ultra-pure water stream, and wherein such unitary housing comprises an outlet for discharging said ultra-pure water stream therefrom. Examples of such treatment systems are reverse osmosis filtering devices.

It is, however, in such also possible to exchange a water membrane of the invention with other membranes comprising functional aquaporins, e.g. the aquaporin containing membranes taught in US 2004/049230. It is believed that such water treatment systems and filter devices as described herein are inventive in their own right, irregardless of the exact nature of the aquaporin containing membrane.

Thus, the invention also includes a reverse osmosis water filtering device for the production of desalinated water from a salt water source, said desalinated water being useful for irrigation agriculture and/or as potable water, wherein at least one of a final reverse osmosis filtering membrane(s) has been replaced by a water membrane comprising functional aquaporin water channels, such as a membrane of the invention. Similarly, the invention also includes a reverse osmosis water filtering device for the production of ultra-pure water from a crude water source said ultra-pure water being useful in the semi-conductor industry and/or in the pharmaceutical industry, wherein at least one of a final reverse osmosis filtering membrane(s) has been replaced by such a water membrane a water membrane comprising functional aquaporin water channels. Also, the invention relates to a reverse osmosis water filtering device for the production of pure water from a crude water source useful in the municipal water industry, chemical industry, drinking water industry, food industry, electronic industry, oil and gas industry, refineries industry, pulp and paper industry, metal industry, mining industry, and power industry, wherein at least one of a final reverse osmosis filtering membrane(s) has been replaced by such a water membrane comprising functional aquaporin water channels. Typically, an osmotic pressure is applied to the downstream side of said water membrane in order to drive the flow of water. The osmotic pressure is typically derived from a concentrated solution having greater osmotic pressure than the water source to be purified.

The invention also relates to a water filtering device for extracting and recovering water from body fluids, such as urine, milk and sweat/perspiration, comprising a water membrane comprising functional aquaporin water channels, such as a water membrane of the invention.

The water purification system/filtering device of the present invention can further comprise a particle filtration module upstream of the water membrane unit, for pre-treating the water stream and removing at least a portion of particulate contaminants therefrom.

Such a particulate filtration module functions to reduce the burden of the downstream water filtration unit, so that less pressure is required for sufficient flow of the water stream, thereby enhancing the energy consumption of the overall system and the operation efficiency thereof.

The particulate filtration module preferably comprises one or more filtration elements selected from the group consisting of (a) hollow fiber membrane separators, and (b) ultrafiltration elements. Multiple hollow fiber membrane separators and ultrafiltration elements can be employed in an alternating manner, so as to maximize the particulate removal capacity of such particular filtration module.

The filtration elements preferably comprise tangential flow or cross-flow filtration devices, as are well known in the art, so as to prevent blinding of the filtration surface.

In order to reduce the vulnerability of such a particulate filtration module to failure of individual filters, and to reduce the system downtime during cleaning and maintenance of individual filters, such particulate filtration module preferably comprises multiple parallelly arranged filtration elements, each of which provides an independent filtration path for the water stream.

A preliminary filter upstream of such particulate filtration module is preferably employed, which can for example have a porosity in a range of from about 10 µm to about 20 µm, so as to filter out large particles (such as solid particles, spores, and bacteria) from the water stream and to extend the life of the filters used in the downstream particulate filtration module.

Such contamination removal unit may comprise either a nanofiltration (NF) module or a reverse osmosis (RO) module for removing ions from the water stream. RO module has been conventionally used for such purpose and proven to be effective. Moreover, nanofiltration requires less pressure and less energy and water consumption in comparison with RO modules.

The water treatment system of the present invention can further comprise a hydraulic accumulator tank, into which the treated water is flowed, for purpose of maintaining an even pressure in the system and providing a substantially constant water supply to the downstream water consumption facility.

The water treatment system of the present invention can further comprise a water quality monitoring module, which continuously monitors one or more variables (e.g., including but not limited to: chlorine concentration, pH value, conductivity, total organic carbon, dissolved oxygen, chemical oxygen demand, turbidity, and radioactivity) that are indicative of the quality of the water stream to be treated, compares such variables against a baseline value determined by previously observed values of such variables, identifies a significant deviation from such baseline value, and produces an output signal indicative of said deviation. Automatic sensors can be used to make accurate measurements of such variables, and a sampler can be used to collect discrete water samples on a regular basis, which allows the isolation of a sample from the time frame when a deviation occurred. Various analytical procedures can then be carried out upon such sample, so as to identify the contaminants in the water that causes such deviation. This water quality monitoring module can further function to turn on or turn off the water treatment system as needed, and/or to alert authorities that the water quality is not meeting pre-established drinking water quality standards.

The water treatment system of the present invention can be either fixed or portable. It is preferably constructed and arranged for vehicular transport and deployment, so it can be used to provide water supply to remote sites.

The system of the present invention is capable of being configured with various components in a parallel and/or serially redundant manner, so as to raise the system reliability and the overall system performance. It will be further recognized that the system and embodiments described herein may employs functional redundancy in effecting complete removal of contaminants from water.

The system/water filtering device is useful for purifying water, and the invention does, as mentioned above, also relate to methods of preparing purified water, where said methods comprise that water is passed through a system/device of the invention. The thus obtained water will e.g. be essentially free from ions, particles, organic matter and colloids, since such moieties have been retained in the device.

Hydrophobic Films of the Invention

As appears from the disclosure above of the 2nd aspect of the invention, i.e. the water membrane which may comprise a hydrophobic material in an intermediate supporting layer flanked by lipid monolayers, it is possible to prepare a material in the form of a hydrophobic film comprising evenly distributed perforations having a uniform shape and size. Such hydrophobic films are believed to be inventive in their own right.

Hence, the invention also pertains to a hydrophobic polymer film comprising multiple perforations, wherein said perforations are evenly distributed in the film and substantially all of substantially the same geometric shape in the intermediate plane between the 2 surfaces of the film. When such perforations each has an aperture area sufficiently large to allow passage of water vapour but sufficiently small to prevent passage of liquid water, such as an area in the range between $100 \text{ nm}^2$-$1 \text{ mm}^2$, the film will function in a manner equivalent to materials such as Goretex®, i.e. the film is breathable but nevertheless water-proof. It is believed that the films of the present invention are superior to materials such a Goretex® films, because the size and geometry of the perforations are under superior control.

The term "hydrophobic film" in the present context denotes a substantially planar, hydrophobic material. The film is typically flexible so that the planar material can attain the form of a curved plane (i.e. if the material is wound around an axis), thus making the hydrophobic film suitable as part of a fabric in clothing and other flexible structures.

The perforations typically have a maximum cross-sectional length in the nm to mm range, such as in the μm range, and the film typically has a thickness in the mm to μm range.

Typically, the geometric shape of the perforations is selected from circular and elliptical. Both shapes are easily obtainable when using laser equipment for introducing the perforations in the film—for instance, circular holes are obtained by using a stand-still laser beam, whereas movement of the film relative to the laser beam (either by moving the film or the laser beam) during exposure will provide an elliptical or even rod-shaped perforation. In preferred embodiments, the perforations all have substantially the same dimensions. The film material is typically selected from the hydrophobic materials discussed above in connection with the disclosure of the $2^{nd}$ aspect of the invention.

While the present invention has been described with reference to specific embodiments thereof, it will be appreciated that numerous variations, modifications, and embodiments are possible, and accordingly, all such variations, modifications, and embodiments are to be construed as being within the spirit and scope of the present invention.

Additional aspects, features and embodiments of the invention will be more fully apparent from the ensuing disclosure and appended claims.

EXAMPLE 1

Reconstitution of AQP-1 in DPPC Lipid Vesicles (Proteoliposomes)

The following protocol has been used to prepare a water membrane according to the invention.

1. Preparation of Small Unilamellar Vesicles (SUVs)
   a. Dry DPPC lipid is suspended in milli-Q water to obtain a concentration of 1,3-1,5 mM.
   b. The suspension is hydrated by incubation at 55° C. for 1 hour resulting in multilamellar vesicles (MLVs)
   c. SUVs are prepared by extruding the MLV solution 12 times through two 100 nm polycarbonate filters
   d. The SUV solution is stored at 55° C.

Figure 9:
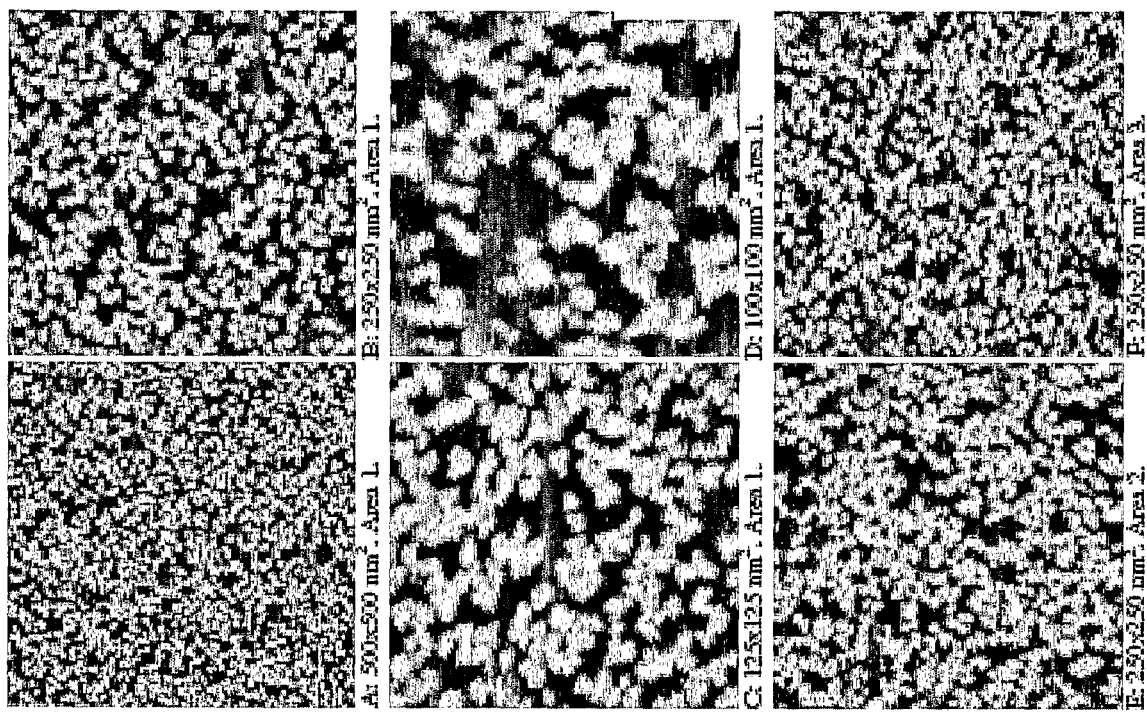
FIG. 9 is an atomic force microscope picture of membranes formed on mica. The membranes have been prepared according to the protocols described in Example 1.

2. Preparation of BioBeads™ (Polystyrene Beads)
   a. Approx. 4 g BioBeadsTm are rinsed 5 times with milli-Q water
   b. The rinsed BioBeadsTm are sonicated for 1 hour under water suction 3. Reconstitution
   a. An appropriate volume of the SUV solution is pipetted into an eppendorf tube
   b. 50 μl 20% Triton X-100 is added
   c. 10 μl AQP-1 in denaturated form in a phosphate buffer purified according to the method described by Zeidel et al. (1992) (conc. 0.5 mg/ml) is added
   d. Milli-Q water is added to a final volume of 200 μl
   e. The solution is incubated at room temperature while shaking for 15 min
   f. Approx. 75 mg rinsed BioBeads are added to the solution which is then incubated while shaking for 30-45 min
   g. The solution in pipetted into a clean eppendorf tube
   h. Steps f.-g. are repeated 3 times (4 times BioBeads in total)
   i. The proteoliposome solution is now ready for use FIG. 9 shows atomic force microscopy (AFM) pictures of DPPC membranes on muscovite, and show an AFM picture of reconstituted AQP1 in DPPC membranes showing that the reconstitution works and that supported bilayers of the resulting vesicles have been made. The area of the small circular structures in the images is approximately 36 nm2 as measured in the images. This corresponds well with the protein surface area in the lipid bilayer. On average (6 images of different sizes from three different areas) the protein covers 48% of the surface, and the lipid 52%. Assuming a lipid area of 0.5 nm2 the calculated lipid-to-protein ratio (LPR) is 77. The supported bilayers were made by vesicle fusion of proteoliposomes prepared with an LPR of 50.

EXAMPLE 2

Formation of Lipid Bilayer and Possibly Further Multiple Bilayers on Porous Muscovite Mica to Obtain a Water Membrane as Schematically Illustrated by FIG. 1

1. A piece of muscovite mica (appr. 1 cm$^2$) is cleaved with tape.
2. Immediately after cleavage 25 µl of the proteoliposome solution from Example 1 is applied to the mica surface.
3. The sample is incubated for 10 minutes at room temperature (21° C.) to form the fused bilayer.
4. After incubation the sample is rinsed 7 times with Milli-Q water to remove excess unbound vesicles.
5. Finally a freshly cleaved second piece of muscovite mica is deposited on the formed lipid bilayer.

EXAMPLE 3

Reconstitution of AQP-1 in *E. Coli* Lipid Extract Vesicles

*E. coli* total lipid extract in chloroform was obtained from Avanti Polar Lipids, (Alabaster, Ala.). Solvents (Chloroform, Ethanol, Methanol, Decane) were all purchased from Sigma-Aldrich (St. Louis, Mo.). SM-2 BioBeads were purchased from BioRad Laboratories (Hercules, Calif.). The water used in all preparations was ultrapure Milli-Q water (18.2 MΩcm-1). Aquaporin-1 purified from bovine erythrocytes was obtained as a suspension of unfolded protein from Dr. Jan Enghild, University of Aarhus.

Chloroform was evaporated from the lipid solution and the dry lipid film was hydrated with 100 mM KCl for 30 min. at 55° C. The solution was vortexed, and small unilamellar vesicles (SUVs) were formed by passing the solution 12 times through two 100 nm polycarbonate filters in a Lipex extruder (Northern Lipids, Vancouver, CD). The reconstitution mixture was prepared by adding Triton X-100 (Sigma) to a final concentration of 1.25% (wt/vol) followed by AQP-1 to a lipid-to-protein ratio (LPR) of 1000:1. Proteoliposomes were formed by removing the detergent. This was done by adsorption to hydrophobic BioBeads (SM-2). The proteoliposomes were used either on the day of preparation or the following day. The solution was stored at 4° C. between experiments.

EXAMPLE 4

Formation of Planar Bilayers and Voltage-clamp Studies: AQP-1 Incorporated Into Lipid Bilayers Without Increasing Ionic-Conductance A voltage-clamp controls (or "clamps") bilayer (or cell membrane) potential V at any desired level. The method used here measures the potential across a brayer formed at a partition between two aqueous solutions. An AgCl-coated silver electrode is placed in one chamber, and electronically compares this voltage to the voltage to be maintained (called the command voltage). The clamp circuitry then passes a current back into the other chamber though another electrode. This electronic feedback circuit holds the transbilayer potential at the desired level, even in the face of permeability changes. Most importantly, the device permits the simultaneous measurement of the current I needed to keep the transbilayer potential at a given voltage. Therefore, the voltage clamp technique indicates how membrane potential influences ionic current flow across the membrane. This influence is expressed in a current-voltage (I/V) relation.

Planar bilayers were formed from n-decane solutions (2.5% wt/vol) of *E. coli* (Avanti Polar Lipids, Alabaster, Ala.) across a hole (1.3 mm dia.) in a Teflon partition separating two aqueous solutions of unbuffered 0.1 M KCl which were prepared the day of the experiment. Bilayer I/V experiments were done at 22° C. with an AxoPatch200 amplifier (Axon Instruments, Sunnyvale, Calif.) using AgCl coated silver-wires as electrodes. I/V protocols were constructed and data recorded using the Clampex 9.2 software (Axon Instruments, Sunnyvale, Calif.). The data were low-pass filtered at a corner frequency of 500 Hz (–3 dB) using an eight-poled Bessel filter (Frequency Devices, Haverhill, Mass.) and after 16 bit AD-conversion (DigiData 1332A, Axon Instruments, Sunnvale, Calif.) stored on PC (Dell Computers, Austin, Tex.) for analysis. Data were analysed and displayed using ClampFit 9.2 (Axon Instruments, Sunnyvale, Calif.) and OriginPro7.5 (OriginLab, Northhampton, Mass.).

Bilayer formation was monitored using a stereo-microscope (Zeiss) equipped with a cold light source (IntraLux 5000, Volpi, CH). After deposition of lipid at the partition hole, the Newtonian diffraction colors from the lipid multilayers gradually disappeared and after about 10 minutes a transparent 'black' lipid membrane was established, surrounded by a thicker lipid/decane torus. This thinning was also reflected in the temporal development in the root-mean-square of the transbilayer current at zero potential IRMS. Initially IRMS was about 1.6 pA and rose to a steady-state value of about 6 pA indicating that a stable bilayer was formed. The bilayer diameter was about 1200 µm. After bilayer formation, transbilayer currents were obtained using a step protocol in which the potential was stepped from –100 mV to +90 mV in increments of 10 mV. Each step lasted 1000 ms with 1000 ms between steps.

AQP-1 was incorporated into the planar bilayer after addition of AQP-1 containing vesicles to the brayer forming solution (2:1 vol/vol) similar results were obtained.

Incorporation of AQP-1 into lipid bilayers did not change the ionic currents, but it changed the time constants of the AQP-1 containing bilayer compared to control. To a first approximation the latter observation can be interpreted as changes in the effective dielectric constants of the torus and the bilayer. This is likely, as the lower dielectric constant of the AQP-1 protein material compared to hydrocarbon material would give rise to lower time-constants in both bilayer and torus.

EXAMPLE 5

Osmotic Gradient Studies: AQP-1 Incorporated Into Lipid Bilayers Imposed an Osmotic Gradient Leading to an Increase in the Ion Concentration in the Unstirred Layer on the Hypotonic Side After formation of lipid bilayers containing AQP-1, an osmotic gradient driven water flux across the membrane was observed, by measuring changes in the K+ ion concentration in the unstirred layer close to the membrane.

Double-barreled K+ electrodes were constructed using 1.2 mm OD glass capillaries (Corning 120F) according to the technique of Zeuthen.

The electrode voltages from the two barrels were recorded using a DU0773 Amplifier (WPI) interfaced to a PC (Dell Computer, Austin, Tex.) using a 12 bit BioLogic 1401+ AD/DA interface (Biologic, Claix, France).

Recordings were performed with the double-barreled electrode placed in the back (cis) chamber containing 100 mM KCI buffered with 20 mM Tris[hydroxymethyl]-aminomethane hydrochloride (TRIS) (T3253, Sigma, St Louis, Mo.) at pH 7.2. The electrode holder was mounted so it entered the cis chamber in a 450 angle relative to the aqueous solution surface and was manipulated using a hydraulic micromanipulator (David Knopf Instruments, Model 1207B) with a minimal step-length of 0.25 µm. Bilayer formation and the coarse position of the electrode was monitored using a stereo-microscope as described in section 5.3 and recording began 10-20 min after deposition of lipid. The overall accuracy in bilayer-electrode distance was judged to be approximately ±7 pm and absolute distance was judged by means of the large changes in electrode potential upon close contact with the brayer. The osmotic gradient across the brayer was induced by having a front (trans) side KCI solution containing 4 M Urea (452042V, BDH, Poole, UK) buffered with 20 mM TRIS at pH 7.2.

It was observed lipid bilayer incorporated AQP-1 induced a water flow in the presence of a transbilayer osmotic gradient.

AQP-1 incorporated in lipid bilayers increased the concentration of K+ ions with about 8% within 20 µm from the brayer on the hypotonic side in the presence of an osmotic gradient compared to the bulk K+ concentration.

Membranes were able to support 4 M osmotic gradients.

EXAMPLE 6

UPW System Comprising the Membrane According to the Invention

Figure 10:
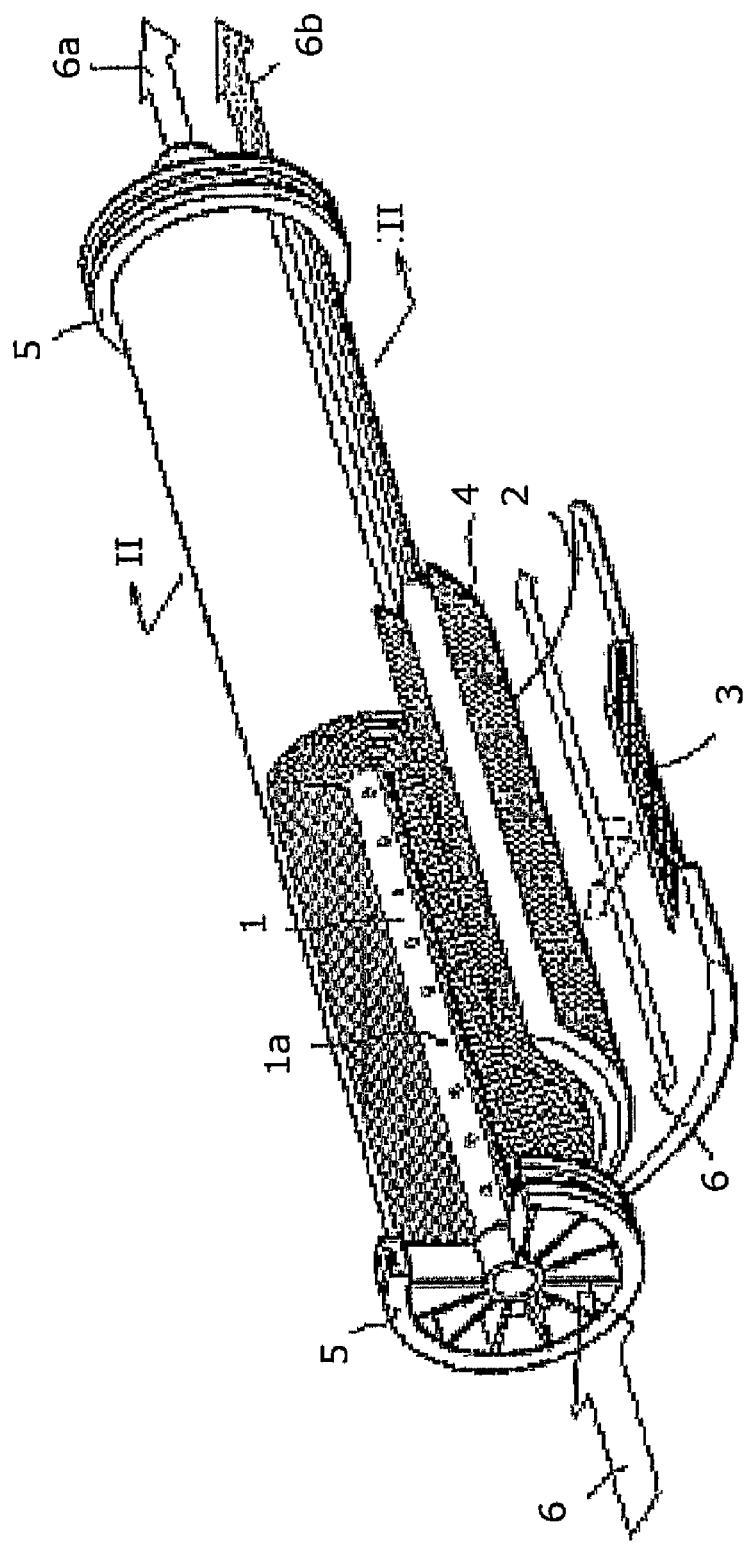
FIG. 10 shows a filtering device comprising spiral wound water membranes of the invention.
Figure 11:
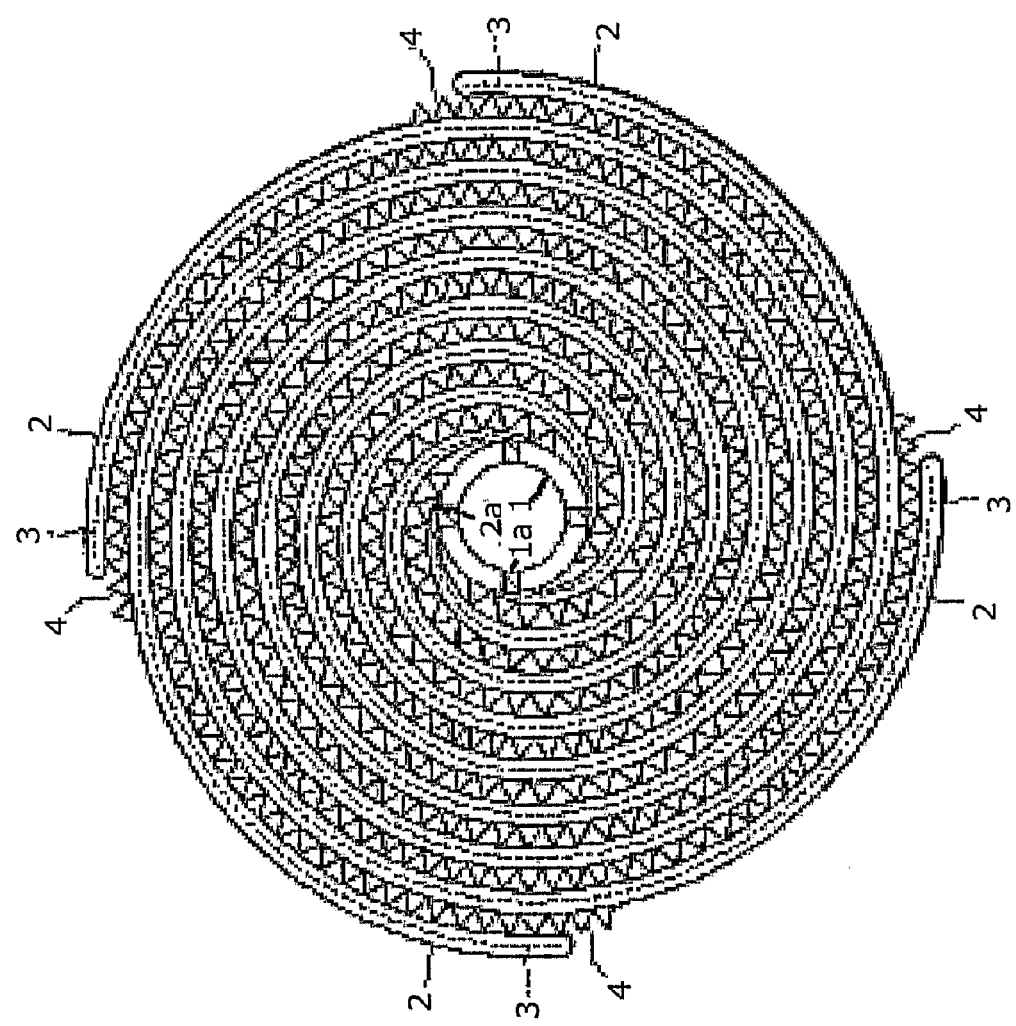
FIG. 11 is a cross sectional view taken along line II--II of FIG. 10.

FIGS. 10 and 11 show a water purification system, according to one embodiment of the present invention. FIG. 10 is a schematic perspective cutaway view of the element, and FIG. 11 is a cross sectional view taken along line II--II of FIG. 10.

The element has a hollow pipe 1 arranged at the center of the element and having a surface thereof formed with a plurality of through-holes 1a. Reverse osmosis membranes 2, permeated liquid passage members 3, and feed liquid passage members 4 are wound around the outer surface of the hollow pipe 1 in a manner described below.

Each reverse osmosis membrane 2 has a bag-like shape as a whole, and a permeated liquid passage member 3 is arranged therein. The bag-shaped reverse osmosis membranes 2 are attached to the outer surface of the hollow pipe 1 with their openings 2a enclosing through-holes 1a formed in the hollow pipe 1 so that the interior of the reverse osmosis membranes 2 and the permeated liquid passage members 3 may communicate with the through-holes 1a.

Each feed liquid passage member 4 is arranged between reverse osmosis membranes 2 associated therewith, and frame members 5 configured to allow liquid to pass therethrough are attached to both ends of the membrane and passage member assembly, whereby the spiral structure is attained.

The above-mentioned element is arranged in a pressure vessel and is adapted to be supplied at its one end (upstream side) with feed liquid 6 at a predetermined pressure.

As the feed liquid 6 flows along the feed liquid passage members 4, it undergoes reverse osmosis separation by the reverse osmosis membranes 2, to be separated into permeated liquid and a solute. The permeated liquid, passing through the reverse osmosis membranes 2 and having a low solute concentration, flows into the through-holes 1a and gathers in the hollow pipe 1. The permeated liquid 6a is then taken out from the downstream side of the element.

The feed liquid which has not passed through the reverse osmosis membranes 2 continues flowing along the feed liquid passage members 4 to the downstream side. In the course of flowing, the feed liquid takes in the solute separated from the feed liquid and left on the membrane surfaces, to become concentrated liquid 6b having a high solute concentration.

There is a critical problem in operating the element such that the element performance lowers due to concentration polarization.

The concentration polarization is a phenomenon that fouling substances, such as impurities and contaminants contained in the feed liquid, are enriched on the membrane surfaces of reverse osmosis membranes 2 which are in contact with feed liquid passage members 4, so that the solute and fouling substance concentration of the feed liquid becomes higher on the membrane surface. As a result, the osmotic pressure becomes higher.

When the concentration polarization occurs, the quantity of permeated liquid decreases, and impurities such as gel and scale precipitate on the membrane surface. For this reason, the reverse osmosis membrane cannot develop its capability and the performance of the element lowers.

The occurrence of the concentration polarization can be suppressed by making the flow of the feed liquid on the membrane surface turbulent. For example, the turbulent flow occurs more easily by using the feed liquid passage member 4 of a smaller thickness to increase the linear velocity of the feed liquid on the membrane surface, so that the concentration polarization layer may be thinned.

With the feed liquid passage member 4 having a smaller thickness, however, the passage defined by the feed liquid passage member 4 is easily clogged with fouling substances contained in the feed liquid such as impurities and microorganisms. As a result, the element performance lowers and the pressure loss in the feed liquid increases. To keep up the quality and quantity of permeated liquid, the operating pressure for the feed liquid needs to be raised, and hence a high-pressure pump requiring electric power to operate and pressure pipes must be provided, resulting in increased liquid production costs.

At least one of the reverse osmosis membranes is a water membrane according to the invention comprising aquaporin and/or aquaglyceroporin channels.

REFERENCES

1. Agre, P., M. Bonhivers, and M. J. Borgnia. (1998). The aquaporins, blueprints for cellular plumbing systems. Journal of Biolgical Chemistry, 273, 14659-14662.
2. Borgnia, M., S. Nielsen, A. Engel, and P. Agre. (1999). Cellular and molecular biology of the aquaporin water channels. Annual Review of Biochemistry, 68, 425-458.
3. A. A. Brian and H. M. McConnell. Allogenic stimulation of cytotoxic T cells by supported planar membranes. Proc. Natl. Acad. Sci. USA, 81:6159-6163, 1984.
4. Burykin and A. Warshel (2003). What really prevents proton transport through aquaporin? Charge self-energy vs. proton wire proposals, Biophysical Journal 85, 3696-3706
5. Chakrabarti, N., Tajkhorshid, E., Roux, B. and Pommes, R. (2004). Molecular basis of proton blockage in aquaporins, Structure 12, 65-74
6. Dainty, J. and C. R. House. 1966. Unstirred layers in frog skin. J Physiol 182:66-78.

7. de Groot, B. L., and Grubmüller, H. (2001). Water permeation across biological membranes: mechanism and dynamics of aquaporin-1 and GlpF, Science 294, 2353-2357.
8. de Groot, B. L., Frigato, T., Helms, V. and Grubmüller, H. (2003). The mechanism of proton exclusion in the aquaporin-1 channel, Journal of Molecular Biology 333, 279-293.
9. Fettiplace, R. and D. A. Haydon. 1980. Water permeability of lipid membranes. Physiol Rev 60:510-50.
10. Fu, D., Libson, A., Miercke, L. J., Weitzman, C., Nollert, P., Krucinski, J., and Stroud, R. M. (2000). Structure of a glycerol-conducting channel and the basis for its selectivity, Science 290, 481-6.
11. Heymann, J. B. and Engel, A. (1999). Aquaporins: Phylogeny, Structure, and Physiology of Water Channels. News Physiol. Sci. (14) p. 188.
12. Ilan, B., Tajkhorshid, E., Schulten, K. and Voth, G. (2004). The mechanism of proton exclusion in aquaporin water channels. PROTEINS: Structure, Function, and Bioinformatics, 55, 223-228.
13. Jensen, M. O., Tajkhorshid, E., and Schulten, K. (2003). Electrostatic tuning of permeation and selectivity in aquaporin water channels, Biophysical Journal 85, 2884-2899.
14. Z. V. Leonenko, A. Carnini, and D. T. Cramb. Supported planar bilayer formation by vesicle fusion: the interaction of phospholipid vesicles with surfaces and the effect of gramicidin on bilayer properties usin atomic force microscopy. Biochim. Biophys. Acta, 1509:131-147, 2000.
15. H. Lin, R. Bhatia, and R. Lal. Amyloid β protein forms ion channels: implications for Alzheimer's disease pathophysiology. FASEB J., 15:2433-2444, 2001.
16. Montal, M. and P. Mueller. 1972. Formation of Biomolecular Membranes from Lipid Monolayers and a Study of Their Electrial Properties. Proc. Nat. Acad. Sci. USA 69:3561-3566.
17. J. Mou, D. M. Czajkowsky, and Z. Shao. Gramicidin A aggregation in supported gel state phosphatidylcholine bilayers. Biochemistry, 35:3222-3226, 1996.
18. Murata, K., Mitsuoka, K., Hirai, T., Walz, T., Agre, P., Heymann, J. B., Engel, A., and Fujiyoshi, Y. (2000). Structural determinants of water permeation through aquaporin-1, Nature 407, 599-605.
19. Pohl, P., S. M. Saparov, and Y. N. Antonenko. 1997. The effect of a transmembrane osmotic flux on the ion concentration distribution in the immediate membrane vicinity measured by microelectrodes. Biophys J 72:1711-8.
20. Preston, G. M., P. Piazza-Carroll, W. B. Guggino, and P. Agre. (1992). Appearance of water channels in Xenopus oocytes expressing red cell CHIP28 water channel. Science, 256, 385-387.
21. E. Reimhult, F. Höök, and B. Kasemo. Intact vesicle adsorption and supported biomembrane formation from vesicles in solution: Influence of surface chemistry, vesicle size, temperature, and osmotic pressure. Langmuir, 19:1681-1691, 2003.
22. Ren, G., Reddy, V. S., Cheng, A., Melnyk, P., and Mitra, A. K. (2001).Visualization of a water-selective pore by electron crystallography in vitreous ice, Proc Natl Acad Sci USA 98, 1398-1403.
23. I. Reviakine and A. Brisson. Formation of supported phospholipid bilayers from unilamellar vesicles investigated by atomic force microscopy. Langmuir, 16:1806-1815, 2000.
24. H. A. Rinia, R. A. Kik, R. A. Demel, M. M. E. Snel, J. A. Killian, J. P. J. M. van der Eerden, and B. de Kruijff. Visualization of highly ordered striated domains induced by transmembrane peptides in supported phosphatidylcholine bilayers. Biochemistry, 39:5852-5858, 2000.
25. Sakmann, B. and E. Neher. 1995. Single channel recording 2 ed. Plenum Press, New York Saparov, S. M. , D. Kozono, U. A. P. Rothe, and P. Pohl. 2001. Water and Ion Permeation of Aquaporin-1 in Planar Bilayers. J. Biol. Chem. 276:31515-31520.
26. A. C. Simonsen and L. A. Bagatolli. Structure of spin-coated lipid films and domain formation in supported membranes formed by hydration. Langmuir, 20:9720-9728, 2004.
27. Sui, H., Han, B. G., Lee, J. K., Walian, P., and Jap, B. K. (2001). Structural basis of water-specific transport through the AQP1 water channel, Nature 414, 872-8.
28. Tajkhorshid, E., Nollert, P., Jensen, M. O., Miercke, L. J., O'Connell, J., Stroud, R. M., and Schulten, K. (2002). Control of the selectivity of the aquaporin water channel family by global orientational tuning, Science 296, 525-530.
29. E. J. M. van Kan, D. N. Ganchev, M. M. E. Snel, V. Chupin, A. van der Bent, and B. de Kruijff. The peptide entibiotic clavanin A interacts strongly and specifically with lipid bilayers. Biochemistry, 42:11366-11372, 2003.
30. Zhu, F., Tajkhorshid, E. and Schulten, K. (2003). Theory and simulation of water permeation in aquaporin-1. Biophysical Journal, 86, 50-57.
31. Zeidel, Mark L., Suresh V. Ambudkar, Barbara L. Smith, and Peter Agre, Biochemistry 1992, 31, 7436-7440.

The invention claimed is:

1. A method for preparing an ultra-pure water filtrate, comprising filtering an aqueous solution through a membrane comprising a sandwich construction having at least two permeable support layers separated by at least one lipid bilayer comprising functional aquaporin water channels, so as to retain ions, particles, organic matter, and colloids, whereby the filtrate is water essentially free from ions, particles, organic matter, and colloids.

2. A method for preparing an ulta-pure water filtrate, comprising filtering an aqueous solution through a membrane comprising a sandwich construction having at least two lipid monolayers, which, when assembled into one bilayer, comprises functional aquaporin water channels, further comprising a hydrophobic perforated material which forms the contact surface with the lipid monolayers and wherein the lipid bilayer is formed in the perforations of the hydrophobic perforated material, so as to retain ions, particles, organic matter, and colloids, whereby the filtrate is water essentially free from ions, particles, organic matter, and colloids.

3. The method according to claim 2, wherein said hydrophobic perforated material is a porous support membrane with a hydrophobic surface, where lipid monolayers assemble on each side and lipid bilayers will assemble in the pores of the porous support membrane, wherein aquaporin water channels can be reconstituted.

4. The method according to claim 2, wherein the hydrophobic material is planar and the perforations are evenly distributed and substantially all of the perforations have substantially the same geometric shape in the intermediate plane between the two surfaces of the hydrophobic material.

5. The method according to claim 2, wherein the perforations have a diameter in the mm to nm range.

6. The method according to claim 5, wherein said perforations each have an aperture area sufficiently large to allow passage of water vapour but sufficiently small to prevent passage of liquid water.

7. The method according to claim 6, wherein said area is between 100 $nm^2$-1 $mm^2$.

8. The method according to claim 2, wherein the geometric shape of the perforations is selected from circular and elliptical.

9. The method according to claim 2, wherein said hydrophobic perforated material consists of a hydrophobic polymer film.

10. The method according to claim 9, wherein the film has a thickness in the mm to μm range.

11. The method according to claim 1 or 2, wherein the lipid bilayer essentially consists of one or more phospholipids.

12. The method according to claim 11, wherein said one or more phospholipids is selected from the group consisting of 1,2-dipalmitoylphosphatidylcholine, phosphoglycerides, sphingolipids, and cardiolipin, and mixtures thereof.

13. The method according to claim 1 or 2, wherein the aquaporin is AQP1.

14. The method according to claim 1 or 2, wherein the aquaporin is of plant origin.

15. The method according to claim 14, wherein the aquaporin is selected from the group consisting of a Tonoplast Intrinsic Protein, a Plasma Membrane Intrinsic Protein, and a Nodulin-26 like Intrinsic Protein aquaporin, and mixtures and hybrids thereof.

16. The method according to claim 1 or 2, wherein the aquaporin water channel is an aquaglyceroporin (GLpF).

17. The method according to claim 16, wherein said GLpF is selected from the group consisting of a GLPA channel, a GLPB1 channel, a GLPB2 channel, a GLPB3 channel, and a GLPY2 channel, and mixtures and hybrids thereof.

18. The method according to claim 1 or 2, wherein said aquaporin is a mutant protein.

19. The method according to claim 1 or 2, wherein said membrane is further encased in a housing to provide a water filtering device.

20. A membrane capable of filtering water, comprising aquaporin water transport proteins that have been reconstituted in lipid vesicles and transformed into a supported layer to form said membrane, wherein the supported layer comprises a hydrophilic membrane surface that comprises cellulose.

21. A method of preparing an ultra-pure water filtrate, comprising filtering an aqueous solution through a membrane comprising aquaporin water transport proteins that have been reconstituted in lipid vesicles and transformed into a supported layer to form said membrane, so as to retain ions, particles, organic matter, and colloids, whereby the filtrate is water essentially free from ions, particles, organic matter, and colloids.

22. The method according to claim 21, wherein the aquaporin is of plant origin.

23. The method according to claim 22, wherein the aquaporin of plant origin is selected from the group consisting of a Tonoplast Intrinsic Protein, a Plasma Membrane Intrinsic Protein, and a Nodulin-26 like Intrinsic Protein, and mixtures and hybrids thereof.

24. The method according to claim 21, wherein the aquaporin water channel is an aquaglyceroporin (GLpF).

25. The method according to claim 24, wherein the GLpF is selected from the group consisting of a GLPA channel, a GLPB1 channel, a GLPB2 channel, a GLPB3 channel, and a GLPY2 channel, and mixtures and hybrids thereof.

26. The method according to claim 21, wherein said aquaporin is a mutant protein.

27. The method according to claim 21, wherein the supported layer comprises a hydrophilic membrane surface, comprising a material selected from the group consisting of mica, mica tape, polysulfon, $Al_2O_3$, and a polymer.

28. The method according to claim 27, wherein the polymer is cellulose.

29. The method according to claim 21, wherein an increased concentration of a solute dissolved in said aqueous solution is obtained.

30. The method according to claim 21, wherein an osmotic pressure is applied to the downstream side of said membrane.

31. The method according to claim 21, wherein an osmotic pressure is derived from a concentrated solution having greater osmotic pressure than the water source to be purified.

32. The method according to claim 31, wherein a high concentration of a non-toxic and easily removable solute is added to a freshwater chamber to encourage regular osmosis across the membrane.

33. A water filtering unit-device comprising a membrane comprising aquaporin water transport proteins that have been reconstituted in lipid vesicles and transformed into a supported layer to form said membrane, wherein said device comprises a multi-layer stacking of individual 2D arrays formed by a series of collapsing vesicles on a supported bilayer and wherein said vesicles are reconstituted with an appropriate aquaporin.

34. A water filtering mesh comprising the unit-device according to claim 33, wherein the stacked unit-device has been incorporated into a stabilizing membrane or a stabilizing polymer matrix.

35. The water filtering unit-device according to claim 33, wherein said individual units have subsequently been stitched via a self-assembly process.

36. The water filtering unit-device according to claim 33, wherein the aquaporin is of plant origin.

37. The water filtering unit-device according to claim 36, wherein the aquaporin of plant origin is selected from the group consisting of a Tonoplast Intrinsic Protein, a Plasma Membrane Intrinsic Protein, and a Nodulin-26 like Intrinsic Protein, and mixtures and hybrids thereof.

38. The water filtering unit-device according to claim 33, wherein the aquaporin water channel is an aquaglyceroporin (GLpF).

39. The water filtering unit-device according to 38, wherein the GLpF is selected from the group consisting of a GLPA channel, a GLPB1 channel, a GLPB2 channel, a GLPB3 channel, and a GLPY2 channel, and mixtures and hybrids thereof.

40. The water filtering unit-device according to claim 33, wherein said aquaporin is a mutant protein.

41. The water filtering unit-device according to claim 33, wherein the supported layer comprises a hydrophilic membrane surface, comprising a material selected from the group consisting of mica, mica tape, polysulfon, $Al_2O_3$, and a polymer.

42. The water filtering unit-device according to claim 41, wherein the polymer is cellulose.

43. The water filtering unit-device according to claim 33, wherein an increased concentration of a solute dissolved in said aqueous solution is obtained.

44. The water filtering unit-device according to claim 33, wherein an osmotic pressure is applied to the downstream side of said membrane.

45. The water filtering unit-device according to claim 33, wherein an osmotic pressure is derived from a concentrated solution having greater osmotic pressure than the water source to be purified.

46. The water filtering unit-device according to claim 45, wherein a high concentration of a non-toxic and easily removable solute is added to a freshwater chamber to encourage regular osmosis across the membrane.

* * * * *